(12) United States Patent
Venkatramani et al.

(10) Patent No.: US 10,101,306 B2
(45) Date of Patent: Oct. 16, 2018

(54) SYSTEMS AND METHODS FOR TWO-DIMENSIONAL CHROMATOGRAPHY

(71) Applicant: Genentech, Inc., South San Francisco, CA (US)

(72) Inventors: Cadapakam Venkatramani, South San Francisco, CA (US); Mohammad Al-Sayah, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 270 days.

(21) Appl. No.: 14/923,273

(22) Filed: Oct. 26, 2015

(65) Prior Publication Data

US 2016/0238573 A1   Aug. 18, 2016

Related U.S. Application Data

(60) Provisional application No. 62/069,219, filed on Oct. 27, 2014.

(51) Int. Cl.
  *G01N 30/46* (2006.01)
  *B01D 15/32* (2006.01)
  (Continued)

(52) U.S. Cl.
  CPC .......... *G01N 30/463* (2013.01); *B01D 15/14* (2013.01); *B01D 15/1878* (2013.01);
  (Continued)

(58) Field of Classification Search
  CPC .......... G01N 30/88; G01N 2030/8813; G01N 2030/8877; G01N 30/74; G01N 30/462;
  (Continued)

(56) References Cited

U.S. PATENT DOCUMENTS 4,845,985 A   7/1989 Berger
5,139,681 A   8/1992 Cortes et al.
(Continued)

FOREIGN PATENT DOCUMENTS

WO   WO-2013/167193 A1   11/2013

OTHER PUBLICATIONS

Stevenson, P. et al. "Comprehensive Two-Dimensional Chromatography With Coupling of Reversed Phase High Performance Liquid Chromatography and Supercritical Fluid Chromatography," *Journal of Chromatography A* 1220:175-178 (2012, e-pub. Nov. 25, 2011).
(Continued)

*Primary Examiner* — Lisa Caputo
*Assistant Examiner* — Suman K Nath
(74) *Attorney, Agent, or Firm* — Morrison and Foerster LLP

(57) ABSTRACT

Provided are two-dimensional chromatography systems and methods for separating and/or analyzing complex mixtures of organic compounds. In particularly, a two-dimensional reversed-phase liquid chromatography (RPLC)-supercritical fluid chromatography (SFC) system is described including a trapping column at the interface which collects the analytes eluted from the first dimension chromatography while letting the RPLC mobile phase pass through. The peaks of interest from the RPLC dimension column are effectively focused as sharp concentration pulses on the trapping column, which is subsequently injected onto the second dimension SFC column. The system can be used for simultaneous achiral and chiral analysis of pharmaceutical compounds. The first dimension RPLC separation provides the achiral purity result, and the second dimension SFC separation provides the chiral purity result (enantiomeric excess).

21 Claims, 27 Drawing Sheets

(51) Int. Cl.
*B01D 15/40* (2006.01)
*G01N 30/88* (2006.01)
*B01D 15/18* (2006.01)
*B01D 15/14* (2006.01)
*G01N 30/74* (2006.01)
*B01D 15/38* (2006.01)

(52) U.S. Cl.
CPC ....... *B01D 15/1885* (2013.01); *B01D 15/325* (2013.01); *B01D 15/3833* (2013.01); *B01D 15/40* (2013.01); *G01N 30/462* (2013.01); *G01N 30/74* (2013.01); *G01N 30/88* (2013.01); *G01N 2030/8813* (2013.01); *G01N 2030/8877* (2013.01)

(58) Field of Classification Search
CPC .. G01N 30/463; B01D 15/3833; B01D 15/14; B01D 15/40; B01D 15/325; B01D 15/1878; B01D 15/1885
USPC ........... 73/61.44, 61.52, 61.53, 61.55, 61.56; 210/198.2, 656; 422/70, 89
See application file for complete search history.

(56) References Cited

U.S. PATENT DOCUMENTS

| | | | |
|---|---|---|---|
| 6,652,753 | B2 | 11/2003 | Berger et al. |
| 6,685,828 | B2 | 2/2004 | Berger et al. |
| 8,419,936 | B2 | 4/2013 | Berger et al. |
| 8,716,025 | B2 | 5/2014 | Witt |
| 8,925,375 | B1 * | 1/2015 | Wiederin ................. G01N 1/38 73/61.55 |
| 2013/0014568 | A1 * | 1/2013 | Lee ........................ G01N 30/10 73/61.56 |
| 2013/0134095 | A1 | 5/2013 | Anderer et al. |

OTHER PUBLICATIONS

International Preliminary Report on Patentability for PCT Application No. PCT/EP2015/074695, dated May 11, 2017, filed Oct. 26, 2015, 14 pages.
International Search Report for PCT Application No. PCT/EP2015/074695, dated Jan. 11, 2016, filed Oct. 26, 2015, 6 pages.
Cortes et al. "On-Line Coupled Liquid Chromatography and Capillary Supercritical Fluid Chromatography: Large-Volume Injection System for Capillary SFC," *J. Microcol. Sep.* 4:239-244, (1992).
Francois et al. "Comprehensive Two-Dimensional Liquid Chromatography Applying Two Parallel Columns in the Second Dimension," *J. Chromatogr. A* 1178:33-42, (2007).
Francois et al. "Construction of a New Interface for Comprehensive Supercritical Fluid Chromatography x Reversed Phase Liquid Chromatography (SFCxRPLC)," *J. Sep. Sci.* 31:3473-3478, (2008).
Francois et al. "Comprehensive Supercritical Fluid Chromatography x Reversed Phase Liquid Chromatography for the Analysis of the Fatty Acids in Fish Oil," *J. Chromatogr. A* 1216:4005-4012, (2009).
Gao et al. "Integration of Normal Phase Liquid Chromatography With Supercritical Fluid Chromatography for Analysis of Fruiting Bodies of *Ganoderma lucidum*," *J. Sep. Sci.* 33:3817-3821, (Dec. 2010).
Giddings. "Two-Dimensional Separations: Concept and Promise,"*Anal. Chem.* 56: 1258A-1260A, (Oct. 1984).
Guibal et al. "Feasibility of Neat Carbon Dioxide Packed Column Comprehensive Two Dimensional Supercritical Fluid Chromatography," *J. Chromatogr. A* 1255:252-258, (Sep. 14, 2012).
Hirata et al. "Technique for Injecting Very Large Volumes In Capillary Supercritical Fluid Chromatography," *J. Microcol. Sep.* 3:17-25, (1991).
Hirata et al. "Development of Comprehensive Two-Dimensional Packed Column Supercritical Fluid Chromatography," *J. Sep. Sci.* 26:531-535, (May 2003).
ICH Expert Working Group. "International Conference on Harmonisation of Technical Requirements for Registration of Pharmaceuticals for Human Use. ICH Harmonised Tripartite Guideline. Impurities in New Drug Substances Q3A(R2)," total pp. 15, (Oct. 2006).
Jandera et al. "Phase System Selectivity and Peak Capacity in Liquid Column Chromatography—The Impact on Two-Dimensional Separations," *Chromatographia* 60:S27-S35, (Jul. 2004).
Lavison et al. "Supercritical Fluid Chromatography and Two-Dimensional Supercritical Fluid Chromatography of Polar Car Lubricant Additives With Neat $CO_2$ as Mobile Phase," *J. Chromatogr. A* 1161:300-307, (Aug. 2007).
Liu et al. "Click Oligo(ethylene glycol)": An Excellent Orthogonal Stationary Phase to C18 for Two-Dimensional Reversed-Phase/Reversed-Phase Liquid Chromatography, *J. Chromatogr. A* 1206:153-159, (Oct. 10, 2008).
Liu et al. "Novel Two-Dimensional Reversed-Phase Liquid Chromatography/Hydrophilic Interaction Chromatography, An Excellent Orthogonal System for Practical Analysis," *J. Chromatogr. A* 1208:133-140, (Oct. 24, 2008).
Louw et al. "Serial Coupling of Reversed-Phase and Hydrophilic Interaction Liquid Chromatography to Broaden the Elution Window for the Analysis of Pharmaceutical Compounds," *J. Chromatogr. A* 1208:90-94, (Oct. 24, 2008).
Lurie. "On—Line Coupled HPLC-Capillary SFC,"*LC GC* 6(12):1066-1067, (Dec. 1988).
Moulder et al. "Coupled Microcolumn Size-Exclusion Liquid Chromatography-Capillary Supercritical Fluid Chromatography," *Analyst* 116:1293-1298, Dec. 1991.
Okamoto et al. "Development of Supercritical Fluid Extraction Coupled to Comprehensive Two-dimensional Supercritical Fluid Chromatography (SFE-SFCxSFC)," *Anal. Sci.* 22:1437-1440, (Nov. 2006).
Song et al. "Reversed-Phase-Reversed-Phase Liquid Chromatography Approach with High Orthogonality for Multidimensional Separation of Phosphopeptides," *Anal. Chem.* 82:53-56, (2010, e-pub. Dec. 1, 2009).
Tian et al. "Multidimensional Liquid Chromatography System With an Innovative Solvent Evaporation Interface," *J. Chromatogr. A*1137:42-48, (Dec. 2006).
Wang et al. "Metabonomics Study on the Effects of the Ginsenoside Rg3 in a β-Cyclodextrin-Based Formulation on Tumor-Bearing Rats by a Fully Automatic Hydrophilic Interaction/Reversed-Phase Column-Switching HPLC-ESI-MS Approach," *Anal. Chem.* 80:4680-4688, (2008, e-pub. May 9, 2008).
Venkatramani et al. "Simultaneous Achiral-Chiral Analysis of Pharmaceutical Compounds Using Two-Dimensional Reversed Phase Liquid Chromatography-Supercritical Fluid Chromatography," *Talanta* 148:548-555, (2016).
Venkatramani et al. "Assessing Stability-Indicating Methods for Coelution by Two-Dimensional Liquid Chromatography With Mass Spectrometric Detection," *J. Sep. Sci.* 37:3214-3225, (Sep. 30, 2014).
Venkatramani et al. "Simultaneous, sequential quantitative achiral—chiral analysis by two-dimensional liquid chromatography," *J. Sep. Sci.*35:1748-1754, (Jul. 2012).
Zeng et al. "Two-Dimensional Supercritical Fluid Chromatography/Mass Spectrometry for the Enantiomeric Analysis and Purification of Pharmaceutical Samples," *J. Chromatogr. A* 1218:3080-3088, (May 20, 2011).
Zhang et al. "Two-Dimensional RPLC-RPLC System with Different pH in Two Dimensions for Separation of alkaloids from Corydalis yanhusuo W. T. Wang," *J. Sep. Sci.* 32:2084-2089, (Jun. 2009).

* cited by examiner

SYSTEMS AND METHODS FOR TWO-DIMENSIONAL CHROMATOGRAPHY

CROSS REFERENCE TO RELATED APPLICATIONS

This application claims priority to U.S. Provisional Patent Application No. 62/069,219, filed Oct. 27, 2014, the disclosure of which is incorporated herein by reference in its entirety.

FIELD OF THE INVENTION

The invention relates to multidimensional chromatography systems and methods for orthogonal separation and analysis of mixtures of compounds. Disclosed are exemplary two-dimensional reversed-phased liquid chromatography-supercritical fluid chromatography systems and methods of use thereof.

BACKGROUND OF THE INVENTION

Chromatography is widely used in separation and analysis of mixtures of compounds. Due to limitations in peak capacity of one-dimensional chromatography, multi-dimensional chromatography systems with significantly increased peak capacity have been devised for the analysis of complex samples. Two-dimensional (2D) chromatographic techniques have become very popular especially in the analysis of complex mixtures. As compared to one-dimensional (1D) chromatography, 2D chromatographic techniques have higher selectivity and resolving power assuming the retention mechanisms are complementary. Maximum peak capacity in a two-dimensional separation system is achieved when the selectivity of the individual separations are independent (orthogonal), so that components which are poorly resolved in the first dimension may be completely resolved in the second dimension. If orthogonal separation mechanisms are used in the two dimensions, the theoretical peak capacity of the system is the product of the individual peak capacities. See Giddings, J. C. *Anal. Chem.* 1984, 56:1258A; Giddings, J. C., in: Cortes, H. J. (Ed.), Multidimensional Chromatography: Techniques and Applications, Marcel Dekker, New York 1990, p. 1; Jandera, P. et al., *Chromatographia* 2004, 60:S27.

However, some restrictions exist for 2D chromatography in terms of sensitivity and solvent compatibilities. For example, the mobile phase that is carried over from the first dimension often creates interference with the second dimension, thus limiting the separation capability of the second dimension. The incompatibility of solvents used in the first and second dimensions can cause severe band dispersion or broadening and peak deterioration, thus posing a big challenge for the interface design. Tian, H., et al., *J. Chromatogr. A* 2006, 1137:42. To alleviate the solvent immiscibility concern, researchers have developed several 2D systems that use compatible mobile phases in both dimensions. Some examples include the following: 2D Reversed Phase Liquid Chromatography (RPLC×RPLC) (Venkatramani, C. J. et al., *J. Sep. Sci.* 2012, 35:1748; Zhang, J. et al., *J. Sep. Sci.* 2009, 32:2084; Song, C. X. et al., *Anal. Chem.* 2010, 82:53; Liu, Y. M. et al., *J. Chromatogr. A* 2008, 1206:153), 2D Hydrophilic Interaction Liquid Chromatography (HILIC×RPLC) (Liu, Y. M. et al., *J. Chromatogr. A* 2008, 1208:133; Wang, Y. et al., *Anal. Chem.* 2008, 80:4680; Louw, S. et al., *J. Chromatogr. A* 2008, 1208:90), 2D Normal Phase Liquid Chromatography×Supercritical Fluid Chromatography (NPLC×SFC) (Gao, L. et al., *J. Sep. Sci.* 2010, 33:3817), and 2D SFC×SFC (Zeng, L. et al., *J. Chromatogr. A* 2011, 1218:3080; Lavison, G. et al., *J. Chromatogr. A* 2007, 1161:300; Hirata, Y. et al., *J. Sep. Sci.* 2003, 26:531; Okamoto, D. et al., *Anal. Sci.* 2006, 22:1437; Guibal, P. et al., *J. Chromatogr. A* 2012, 1255:252). Anderer et al., US 2013/0134095 disclosed a 2D LC system and methods which attempt to further reduce the interference with the second LC by the first LC by controlling the injection event of injecting an output of the first LC into the second LC in relation to the state of the second LC.

One technique that couples the incompatible "normal phase" and "reversed-phase" dimensions is 2D SFC×RPLC (Francois, I. et al., *J. Sep. Sci.* 2008, 31:3473-3478; Francois, I. and Sandra, P. *J. Chromatogr. A* 2009, 1216:4005). In this case, the non-polar supercritical carbon dioxide in the SFC fractions is evaporated off (when exposed to atmospheric pressure) to yield fractions with compatible mobile phases to the second RPLC dimension (usually an alcohol modifier). The SFC×RPLC system of Francois, I. et al. employs a 2-position/10-port switching valve for the interface between the first dimension SFC unit and the second dimension RPLC unit. The system uses packed loops in the interface to prevent the analytes eluted from the SFC column from being forced into the waste line by the $CO_2$ stream, and water is introduced into the loop to reduce interference of residual $CO_2$ gas in the second dimension.

Cortes and co-workers (*J. Microcol. Sep.* 1992, 4:239-244; and U.S. Pat. No. 5,139,681) described a 2D LC×SFC system including a sample inlet capillary where volatile solvents from the first dimension LC is eliminated by passage of nitrogen gas leaving a deposit of the eluted analytes, which is then taken up by the $CO_2$ mobile phase for the second dimension SFC. However, solvent elimination by passage of nitrogen gas is not practical for RPLC which uses aqueous mobile phase.

There remains a need for an efficient chromatography system and methods for separating and analyzing complex samples where it is advantageous to conduct a first dimension RPLC and a second dimension SFC separation.

BRIEF SUMMARY OF THE INVENTION

Disclosed are multi-dimensional chromatography systems and methods for separating and/or analyzing complex mixtures of organic compounds, for example, a two-dimensional reversed-phase liquid chromatography (RPLC)-supercritical fluid chromatography (SFC) system, particularly a RPLC×SFC system including an interface capable of retaining the analytes eluted from the RPLC column while letting the RPLC mobile phase pass through, thus reducing the amount of RPLC solvents carried on to the SFC column.

In one aspect, provided is a chromatography system for separating a sample comprising: (i) a first separation unit comprising: a) a first pump assembly for driving a first mobile phase through the first separation unit, b) a sample injector for introducing a sample to the first separation unit, and c) a reversed-phase liquid chromatography (RPLC) column; (ii) a second separation unit comprising: a) a second pump assembly for driving a second mobile phase through the second separation unit, and b) a supercritical fluid chromatography (SFC) column; and (iii) a first fluidic routing unit comprising a plurality of sample loops, said first fluidic routing unit is connected to the first separation unit and the second separation unit, wherein at least one of the plurality of sample loops comprises a trapping column, said trapping column comprising a stationary phase; and wherein the chromatography system is configured for first separating the sample in the first separation unit and subsequently introducing at least a portion of the sample eluted from the RPLC column to the second separation unit. In some embodiments, the system further comprises detector(s) for the first separation unit and/or the second separation unit. The system may further comprise one or more control devices operably connected to one or more of the system components.

In some embodiments, the 2D RPLC×SFC system comprises a first fluidic routing unit which comprises two sample loops; wherein one of the two sample loops is in fluidic communication with the first separation unit and the other one of the two sample loops is in fluidic communication with the second separation unit. In some embodiments, the first fluidic routing unit comprises three or more sample loops, and wherein one or more of the sample loops is in fluidic isolation from the first separation unit and the second separation unit. In one variation, at least one sample loop that is in fluidic isolation from the first separation unit and the second separation unit comprises a trapping column loaded with a stationary phase material. In some embodiments, the first fluidic routing unit is configured to allow countercurrent elution of analytes retained in a trapping column. In some embodiments, the first fluidic routing unit is configured to allow co-current elution of analytes retained in a trapping column.

In some embodiments, the 2D RPLC×SFC system comprises a second separation unit which comprises one SFC column, and optionally a focus column positioned upstream of the SFC column. In some embodiments, the second separation unit comprises a parallel array of SFC columns, each optionally comprise a focus column positioned upstream of the SFC column.

Further provided are methods of using the chromatography systems described herein. In some embodiments, provided is a method for analyzing a samples (such as a complex sample) using a chromatography system described herein comprising: first separating the complex sample into fractions by RPLC; and further separating the fractions from the RPLC dimension by SFC in the second dimension.

In one embodiment, provided is a method for simultaneous achiral-chiral analysis of a sample comprising a mixture of stereoisomeric components using a chromatography system described herein comprising: separating (or resolving) one or more diastereomeric component(s) of interest in the sample by RPLC in the first dimension, which provides achiral purity of the sample; and separating (or resolving) the enantiomeric pair(s) of interest by SFC in the second dimension in the same analytical run, which further provides chiral purity of the components in the sample.

In another aspect, provided is a method for separating a sample by multi-dimensional chromatography (such as 2D RPLC×SFC) comprising the steps of: (i) capturing at least a portion of a sample on a trapping column, said portion is from separating the sample by reversed-phase liquid chromatography (RPLC), said trapping column comprising a stationary phase; and (ii) subjecting the portion of the sample captured on the trapping column to further separation by supercritical fluid chromatography (SFC).

DETAILED DESCRIPTION OF THE INVENTION

The invention provides efficient chromatography systems and methods for separating and analyzing complex samples, particularly two-dimensional RPLC×SFC systems and methods of use thereof.

The term "a" or "an" as used herein, unless clearly indicated otherwise, refers to one or more.

Reference to "about" a value or parameter herein includes (and describes) embodiments that are directed to that value or parameter per se. For example, description referring to "about X" includes description of "X".

Systems

In one aspect, the invention provides a two-dimensional RPLC×SFC chromatography system for separating a sample, wherein the sample is separated in the first dimension RPLC and then in the second dimension SFC, the system comprising a first separation unit for reversed-phase liquid chromatography, a second separation unit for supercritical fluid chromatography, and an interface which is a fluidic routing unit. The fluidic routing unit comprises multiple sample loops each having a predefined volume that can be placed in the fluidic path of the first separation unit for collecting fractions eluted from the RPLC column. A sample loop in which a fraction has been collected is subsequently placed in the fluidic path of the second separation unit for transferring the fraction collected in the sample loop onto the SFC column for further separation. In a system of the present invention, at least one of the sample loops comprises a trapping column containing a stationary phase for retaining the analytes eluted from RPLC column while letting the mobile phase pass through. The new interface design allows the coupling of RPLC and SFC.

In some embodiments, provided is an online two-dimensional chromatographic system utilizing RPLC in the first dimension and SFC in the second dimension, which can achieve simultaneous achiral and chiral analysis of pharmaceutical compounds. In certain embodiments, the interface comprises a 2-position/8-port switching valve with small volume C-18 trapping columns. The peaks of interest from the first RPLC dimension column were effectively focused as sharp concentration pulses on small volume trapping column(s) (e.g., C-18 trapping column(s)) and then injected onto the second dimension SFC column. The first dimension RPLC separation provides the achiral purity result, and the second dimension SFC separation provides the chiral purity result (enantiomeric excess).

Figure 1:
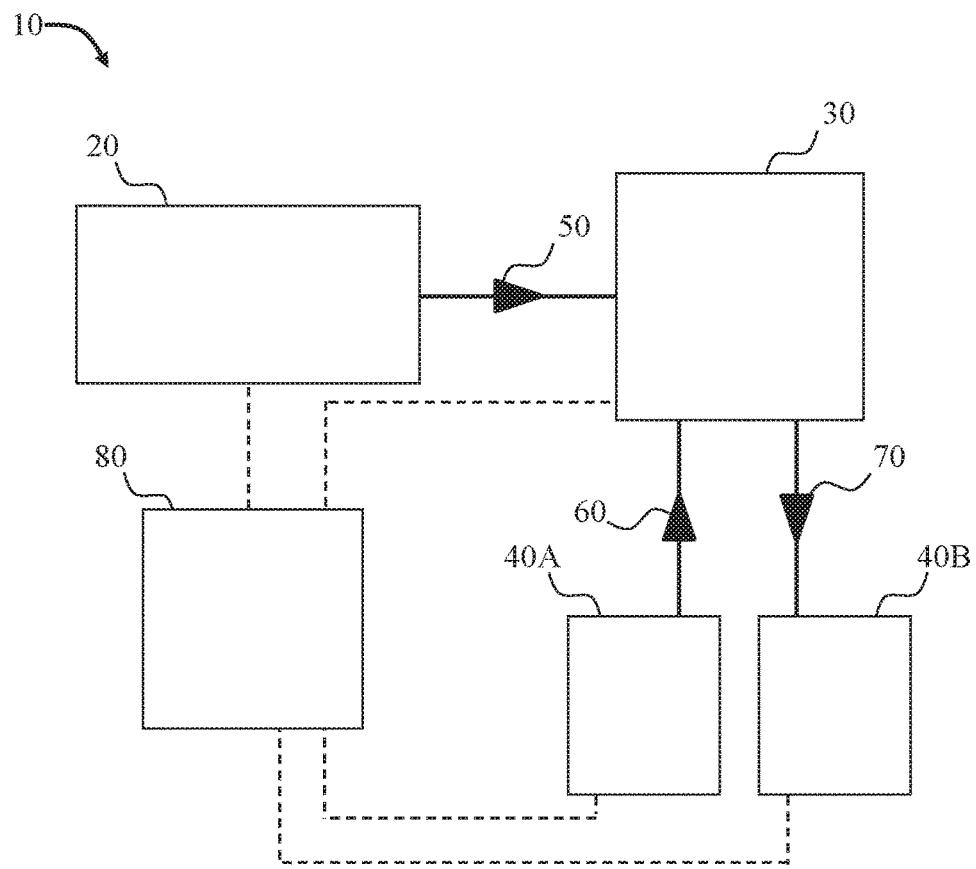
FIG. 1 is a schematic of an exemplary multidimensional chromatography system 10.

Referring to the drawings, FIG. 1 depicts an overview schematic of an exemplary multidimensional chromatography system 10. A first separation unit 20 and a second separation unit 40A and 40B are interfaced with a first fluidic routing unit 30. The directional flow of a first mobile phase through the first separation unit 20 to the first fluidic routing unit 30 is indicated by the arrow 50. A second mobile phase, the directional flow indicated by the arrow 60, travels through the upstream subunit 40A of the second separation unit to the first fluidic routing unit 30 and is subsequently directed back through downstream subunit 40B of the second separation unit in the direction indicated by the arrow 70.

In some embodiments, the system comprises one or more control device operably connected to one or more components of the system for controlling the operation of the system, for example, the pump assemblies, the sample injector, the first fluidic routing unit (interface), and the detectors that are present. The control device may include a computer system equipped with appropriate software for controlling the operation of each of the individual devices and for automated sample analysis (e.g. Agilent's Instrument Control Software or Automation Studio software). Referring to FIG. 1, a control device 80 is operably connected to at least one of the following: the first separation unit 20, the first routing unit 30, and the second separation unit 40A and 40B.

The composition of the mobile phase in chromatography may be kept constant over time, what is known in the art as isocratic mode. Alternatively, the composition of the mobile phase may be varied over time, what is known in the art as gradient mode.

The first separation unit of the 2D RPLC×SFC chromatography system comprises a first pump assembly for driving a mobile phase through the first separation unit, a sample injector for introducing a sample to the first separation unit, and a reversed-phase liquid chromatography (RPLC) column. The mobile phase for RPLC may comprise a two-solvent system (e.g., water-acetonitrile and water-methanol mixtures) and optionally certain additives (e.g., acetic acid, trifluoroacetic acid, formic acid, ammonium hydroxide, ammonium acetate, sodium acetate, and the like). The pump assembly comprises one or more pumps for driving a mobile phase for RPLC. While suitable pumps for liquid chromatography are readily known in the art, in some embodiments, the pump may be a reciprocating pump, a displacement pump, a pneumatic pump, and/or any combination of the at least one of the above. The system may comprise any suitable sample injector for injecting a sample into the mobile phase for RPLC, such as a manual sample injector or an auto-sampler. The RPLC column comprises a reversed-phase stationary phase such as beads of C-18 stationary phase. The reversed-phase stationary phase can be silica-based (for example containing a core structure of silica gel) or polymer-based (for example containing a core structure of an organic polymer (e.g., polystyrene)). Non-limiting examples of materials suitable for reversed-phase stationary phase includes C-18, C-8, C-4, phenyl and phenyl derivatives, polar embedded phase, mixed mode phase, and the like.

In some embodiments, the first separation unit further includes a detector positioned downstream of the RPLC column to detect presence of the analytes eluted from the RPLC column. Any detector suitable for detecting the compounds in the sample may be used, such as a differential refractometer, ultraviolet spectrophotometer, ultraviolet-visible spectrophotometer detector, charged aerosol detector, fluorescence detector, and mass spectrometer. In some embodiments, the detector for the RPLC dimension is an ultraviolet-visible spectrophotometer detector, charged aerosol detector, fluorescence detector, and mass spectrometer.

The detector may be optional in a system where the analytes are eluted at a predetermined time, for example, when the RPLC is run under pre-programmed conditions and the retention time for the analytes of interests are pre-determined.

Figure 2A:
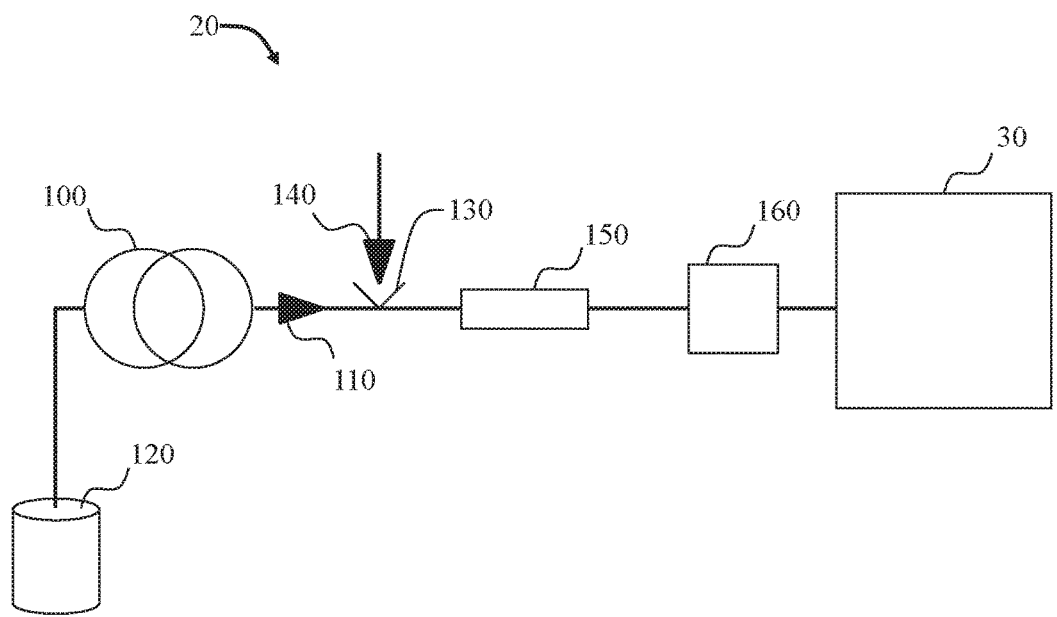
FIG. 2A is a schematic of an exemplary first separation unit 20, interfaced with a first fluidic routing unit 30.

Referring to the drawings, FIG. 2A shows a schematic of an exemplary first separation unit 20 interfaced with the first fluidic routing unit 30. The first separation unit 20 comprises a first pump 100 for driving the first mobile phase through the first separation unit in the direction indicated by the arrow 110. In some embodiments, the first mobile phase may be comprised of only one solvent. In some embodiments, the first mobile phase may be comprised of a plurality of mixed solvents. In some embodiments, mixing of solvents of the first mobile phase may be provided upstream of the pump 100 so that the pump 100 receives the mixed solvent as the first mobile phase. In some embodiments the first mobile phase is stored in a receptacle 120. In some embodiments, the pump 100 may be comprised of a plurality of individual pumping units, with plural of the pumping units each receiving and pumping a different solvent or mixture of solvents so that mixing occurs downstream of the pump 100. In some embodiments, the first mobile phase may further comprise one or more additives. Non-limiting examples of additives used in RPLC mobile phase include phosphoric acid, phosphate buffers, acetic acid, trifluoroacetic acid, formic acid, ammonium hydroxide, ammonium acetate, sodium acetate, alkyl sulfonates, and the like.

In some embodiments, the composition of the first mobile phase may be kept constant over time (running in isocratic mode). In some embodiments, the composition of the first mobile phase may be varied over time (running in gradient mode). Operation in the gradient mode typically requires two pumps—one for driving the more polar solvent in the mobile phase (e.g. water); the other for driving the less polar solvent (e.g., acetonitrile or methanol). Operation in the isocratic mode may employ a system with two pumps delivering two solvents at a constant ratio, or a system with one pump driving a pre-mixed mobile phase.

Furthermore, the schematic of FIG. 2A illustrates a sample injector 130 located between the pump 100 and a reversed-phase liquid chromatography (RPLC) column 150. The sample injector 130 introduces the sample to the first separation unit in the direction indicated by the arrow 140. In some embodiments, the sample injector 130 is provided to add a sample to the first separation unit. In some embodiments, the sample injector 130 may comprise a valve and a sample loop for introducing the sample to the first separation unit. In some embodiments, the sample injector 130 may comprise an autosampler.

As shown in the schematic of FIG. 2A, the RPLC column 150 is located downstream of the sample injector 130. The RPLC column 150 may comprise a reversed-phase stationary phase. In some embodiments, the RPLC column 150 may comprise a carbon chain-bonded silica gel. In some embodiments, the carbon chain-bonded silica gel may comprise a carbon chain that is 18 carbons in length (i.e., C18-reversed-phase silica gel). In some embodiments, the carbon chain-bonded silica gel may comprise a carbon chain that is 8 carbons in length (i.e., C8-reversed-phase silica gel). In some embodiments, the carbon chain-bonded silica gel may comprise a carbon chain that is 4 carbons in length (i.e., C4-reversed-phase silica gel). In some embodiments, the reversed-phase stationary phase may comprise a hydrocarbon chain bonded to a polymer core such as an organic polymer (e.g., polystyrene).

In some embodiments, the temperature of the RPLC column 150 may be maintained at a selected temperature. In some embodiments, the temperature of the RPLC column 150 may be maintained at a range of about 10° C. to about 50° C. In some embodiments, the temperature of the RPLC column 150 may be maintained at about 40° C.

Optionally located between the RPLC column 150 of the first separation unit 20 and the first fluidic routing unit 30 is a first detector 160 (FIG. 2A). The first detector measures the presence of at least a portion of the sample eluted from the RPLC column 150. In some embodiments, the first detector 150 is an optical detector. In some embodiments, the first detector 150 is a spectrophotometric detector. In some embodiments, the first detector 150 is selected from one or more of the following: ultraviolet spectrophotometer, ultraviolet-visible spectrophotometer detector and fluorescence detector.

The second separation unit of the 2D RPLC×SFC chromatography system comprises a second pump assembly for driving a second mobile phase through the second separation unit and a supercritical fluid chromatography (SFC) column. The mobile phase for SFC comprises a supercritical fluid (e.g., supercritical carbon dioxide) and a modifier or co-solvent (e.g., methanol, ethanol, and isopropyl alcohol), optionally one or more additives (e.g., ammonium hydroxide). The second pump assembly comprises one or more pumps for driving the supercritical fluid mobile phase. Any stationary phase suitable for SFC may be used in the SFC column. The choice of the stationary phase material may depend on the separation criteria for the second dimension. In some embodiments, the SFC column comprises a normal phase stationary phase such as silica gel. In some embodiments, the chromatography system further comprises a detector positioned downstream of the SFC column for detecting the presence of analytes eluted from the SFC column. Any detectors suitable for SFC may be used, such as a UV detector, a photodiode array detector, charged aerosol detector, fluorescence detector, and a mass spectrometer (MS).

Figure 2B:
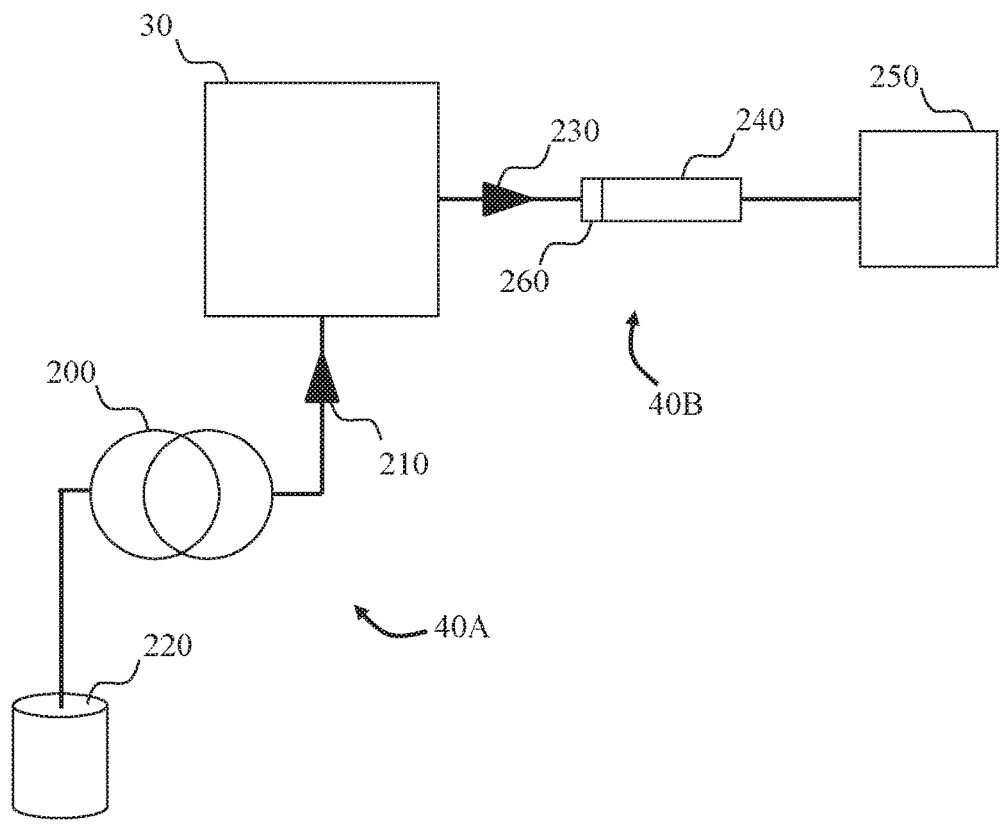
FIG. 2B is a schematic of an exemplary second separation unit 40A and 40B interfaced with a first fluidic routing unit 30.

Referring to the drawings, FIG. 2B depicts a schematic of an exemplary second separation unit, comprising an upstream subunit 40A and a downstream subunit 40B, interfaced with the first fluidic routing unit 30. The upstream subunit 40A of the second separation unit comprises a second pump 200 for driving a second mobile phase through the second separation unit 40A and 40B in the direction indicated by the arrow 210. The downstream subunit 40B of the second separation unit comprises an SFC column 240, and optionally a focus column 260 and/or a detector 250. In some embodiments, the second mobile phase may be comprised of only one solvent. In some embodiments, the second mobile phase may be comprised of a plurality of mixed solvents. In some embodiments, mixing of solvents of the second mobile phase may be provided upstream of the pump 200 so that the pump 200 receives the mixed solvents as the second mobile phase. In some embodiments, the second mobile phase is stored in a receptacle 220. In some embodiments, the pump 200 may be comprised of a plurality of individual pumping units, with plural of the pumping units each receiving and pumping a different solvent or mixture of solvents so that mixing occurs downstream of the pump 200.

In some embodiments, the composition of the second mobile phase may be kept constant over time (running in isocratic mode). In some embodiments, the composition of the second mobile phase may be varied over time (running in gradient mode). While suitable pumps for supercritical fluid chromatography are readily known in the art, in some embodiments, the pump may be a reciprocating pump, a displacement pump, a pneumatic pump, and/or any combination of the at least one of the above.

As shown in FIG. 2B, the upstream subunit 40A of the second separation unit is interfaced with the first fluidic routing unit 30 downstream of the pump 200. The directional flow of the second mobile phase through the downstream subunit 40B of the second separation unit downstream of the first fluidic routing unit 30 is shown by the arrow 230. The SFC column 240 may comprise a normal phase stationary phase. In some embodiments, the normal phase stationary phase is silica. In some embodiments, the normal phase stationary phase is silica modified with cyanopropyl functional groups. In some embodiments, the normal phase stationary phase is silica modified with aminopropyl functional groups. In some embodiments, the normal phase stationary phase is silica modified with ethyl pyridine functional groups. In some embodiments, the normal phase stationary phase is silica modified with sulfonic acid and/or phenyl functional groups. In some embodiments, the normal phase stationary phase is silica modified with 1,2-dihydroxypropyl propyl ether functional groups. In some embodiments, the normal phase stationary phase is a polymer, such as an organic polymer (e.g., polystyrene), modified with a functional group (e.g., a cyanopropyl, aminopropyl, ethyl pyridine, sulfonic acid, phenyl, or 1,2-dihydroxypropyl propyl ether functional group). Other examples of materials suitable for use in the stationary phase for SFC include silica, ethyl pyridine, cyano, epic diol, pyridyl amide, nitro, and the like.

In some embodiments, the temperature of the SFC column 240 may be maintained at a selected temperature. In some embodiments, the temperature of the SFC column 240 may be maintained at a range of about 35° C. to about 45° C. In some embodiments, the temperature of the SFC column 240 may be maintained at about 40° C.

Referring to FIG. 2B, in some embodiments, an optional focus column 260 is located upstream of the SFC column 240. The focus column 260 comprises a stationary phase. In some embodiments, the stationary phase may comprise a reversed-phase stationary phase. In some embodiments, the reversed-phase stationary phase may comprise a carbon chain-bonded silica gel. In some embodiments, the carbon chain-bonded silica gel may comprise a carbon chain that is 18 carbons in length (i.e., C18-reversed-phase silica gel). In some embodiments, the carbon chain-bonded silica gel may comprise a carbon chain that is 8 carbons in length (i.e., C8-reversed-phase silica gel). In some embodiments, the carbon chain-bonded silica gel may comprise a carbon chain that is 4 carbons in length (i.e., C4-reversed-phase silica gel). In some embodiments, the reversed-phase stationary phase may comprise a carbon chain (such as a C-18, C-8 or C-4 chain) bonded to a polymer core such as an organic polymer (e.g., polystyrene). In general focus column will match the reverse phase used in the primary dimension and/or the trapping column used in the interface.

In some embodiments, the temperature of the focus column 260 may be maintained at a selected temperature. In some embodiments, the focus column may be maintained at the same temperature as the SFC column. In some embodiments, the temperature of the focus column 260 may be maintained at about 35° C. to about 45° C. In some embodiments, the temperature of the focus column 260 may be maintained at about 40° C.

Located downstream of the SFC column 240 is a second detector 250 (FIG. 2B). The detector measures the presence and amounts of analytes eluted from the SFC column 240. In some embodiments, the second detector 250 is an optical detector. In some embodiments, the second detector 250 is a spectrophotometric detector. In some embodiments, the second detector 250 is selected from one or more of the following: differential refractometer, ultraviolet spectrophotometer, ultraviolet-visible spectrophotometer detector, fluorescence detector, and infrared spectrophotometer. In some embodiments, the second detector 250 is a mass spectrometer. In some embodiments, the mass spectrometer may be selected from one or more of the following: a sector instrument, a quadrupole mass filter instrument, a time-of-flight instrument, an ion-trap instrument, a quadrupole ion trap instrument, a linear quadrupole ion trap instrument, an orbitrap instrument, a Fourier transform ion cyclotron resonance instrument, and any combination or hybrid of the listed instrument types. As is well known in the art, the sample is introduced into the mass spectrometer via ionization techniques, such as, but not limited to, fast atom bombardment, chemical ionization, atmospheric-pressure chemical ionization, electrospray ionization, and nano-electrospray ionization. In some embodiments, the sample is introduced into the mass spectrometer via atmospheric-pressure chemical ionization or electrospray ionization.

In some embodiments, the downstream portion of the second separation unit 40B may further comprise a fraction collector in place, after, or in parallel with the second detector.

Optionally, in some embodiments, a control device 80 is operably connected to at least one of the following: a pump 100 and/or 200, a sample injector 130, a first detector 160, the first fluidic routing unit 30, and a second detector 250.

The interface between the two dimensions in a 2D chromatography system controls routing of analytes separated and eluted from the first dimension into the second dimension for further separation and determines the mode of operation. The 2D chromatography system of the present invention is configured for first separating the sample in the first separation unit by RPLC and subsequently introducing at least a portion of the sample eluted from the RPLC column to the second separation unit for further separation by SFC.

The first fluidic routing unit comprises a plurality of sample loops, said first fluidic routing unit is connected to the first separation unit and the second separation unit, wherein at least one of the plurality of sample loops comprises a trapping column, said trapping column comprising a stationary phase. The stationary phase material in the trapping columns may be the same as the stationary phase material used in the RPLC column or different from the stationary phase material used in the RPLC column. In some embodiments, the stationary phase used in the trapping column may comprise a reversed-phase stationary phase. In some embodiments, the reversed-phase stationary phase may comprise a carbon chain-bonded silica gel. In some embodiments, the carbon chain-bonded silica gel may comprise a carbon chain that is 18 carbons in length (i.e., C18-reversed phase silica gel). In some embodiments, the carbon chain-bonded silica gel may comprise a carbon chain that is 8 carbons in length (i.e., C8-reversed phase silica gel). In some embodiments, the carbon chain-bonded silica gel may comprise a carbon chain that is 4 carbons in length (i.e., C4-reversed phase silica gel). In some embodiments, the reversed-phase stationary phase may comprise a carbon chain (such as a C-18, C-8 or C-4 chain) bonded to a polymer core such as an organic polymer (e.g., polystyrene).

The first fluidic routing unit in some embodiments includes a routing mechanism (such as a switch valve) comprising a plurality of ports, channels allowing liquid to flow between the ports and sample loops connected to the ports. In some embodiments, the routing mechanism is a 2-position/8-port switching valve. In some embodiments, the routing mechanism is a 2-position/10-port switching valve. In some embodiments, the routing mechanism is a 2-position/4-port duo valve. In some embodiments, the routing mechanism is a 2-position 8-port or 10-port switching valve.

In some embodiments, the first fluidic routing unit of the 2D RPLC×SFC system comprises two sample loops; wherein one of the two sample loops is in fluidic communication with the first separation unit and the other one of the two sample loops is in fluidic communication with the second separation unit. In some embodiments, one of the two sample loops comprises a trapping column comprising a stationary phase. In some embodiments, both sample loops each comprise a trapping column comprising a stationary phase.

Figure 3A:
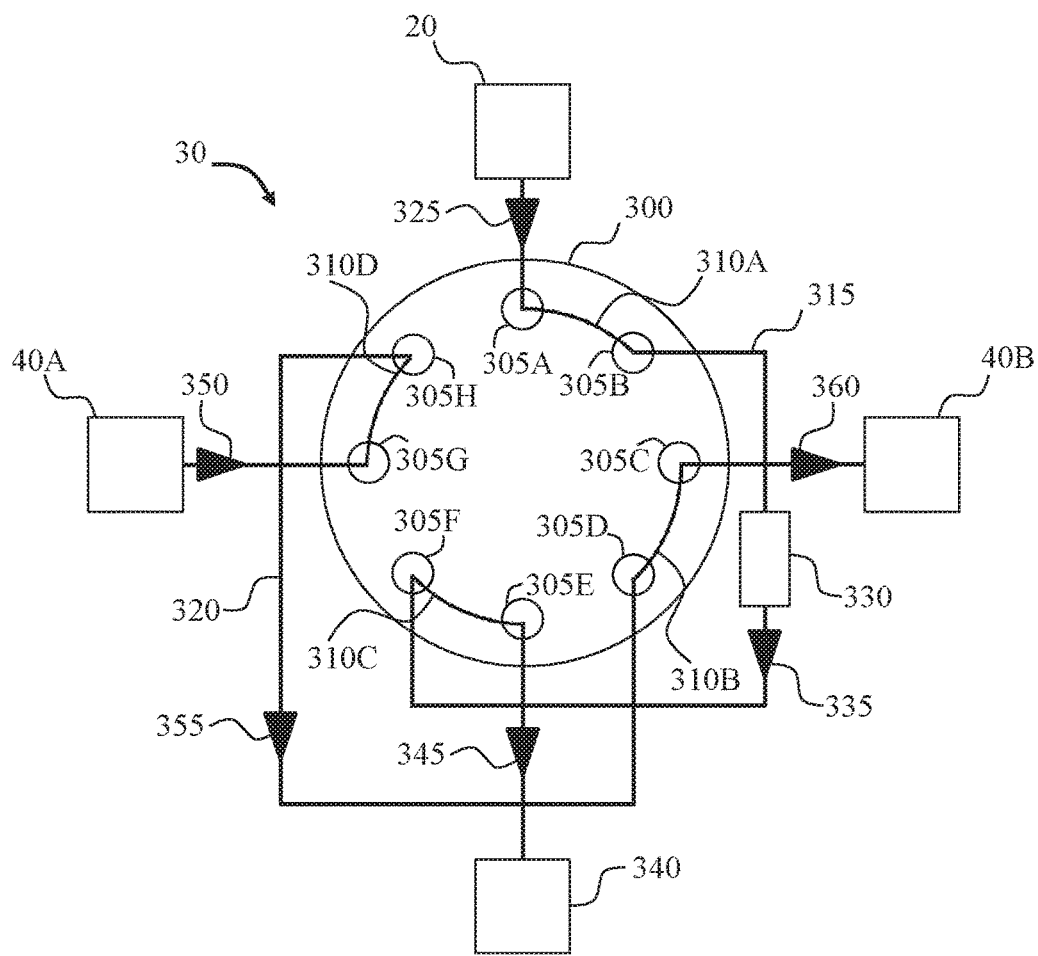
FIG. 3A and FIG. 3B are schematics of an exemplary first fluidic routing unit 30 comprising a trapping column 330, wherein the configuration of the first fluidic routing unit 30 is configured for countercurrent flow of the first mobile phase and second mobile phase through said trapping column 330.

FIG. 3A depicts a schematic of an exemplary first fluidic routing unit 30 interfaced with the first separation unit 20 and the second separation unit 40A and 40B. In this instance, the interface fluidic routing unit includes a routing mechanism 300, which in one variation is a 2-position/8-port switching valve, comprising a plurality of ports 305A-305H, a plurality of channels 310A-310D, and two sample loops, 315 and 320. As shown in FIG. 3A, the plurality of channels 310A-310D are shown in the first of two possible configurations.

As exemplified in FIG. 3A, the first separation unit 20 is connected to the routing mechanism 300 at port 305A. The first mobile phase is driven through the first separation unit 20 in the direction indicated by the arrow 325 and the routing mechanism 300 directs the first mobile phase to a sample loop 315 by way of the channel 310A. The sample loop 315 is connected to the routing mechanism 300 at port 305B and port 305F. The sample loop 315 comprises a trapping column 330, said trapping column comprises a stationary phase.

The routing mechanism 300 directs the first mobile phase to a downstream receptacle 340, in the direction indicated by the arrow 345, by way of a channel 310C. In some embodiments, the downstream receptacle 340 is a waste receptacle. In some embodiments, the downstream receptacle 340 is a fraction collector.

As depicted in FIG. 3A, the upstream subunit 40A of the second separation unit is connected to the routing mechanism 300 at port 305G. The second mobile phase is driven through the second separation unit 40A in the direction indicated by the arrow 350 and the routing mechanism 300 directs the second mobile phase to a sample loop 320 by way of a channel 310D. The sample loop 320 is connected to the routing mechanism 300 at port 305H and port 305D, wherein the first mobile phase travels in the direction indicated by the arrow 355. The routing mechanism 300 is connected to the downstream subunit 40B of the second separation unit via port 305C. The routing mechanism 300 directs the second mobile phase through the downstream subunit 40B of the second separation unit in the direction indicated by the arrow 360.

Figure 3B:
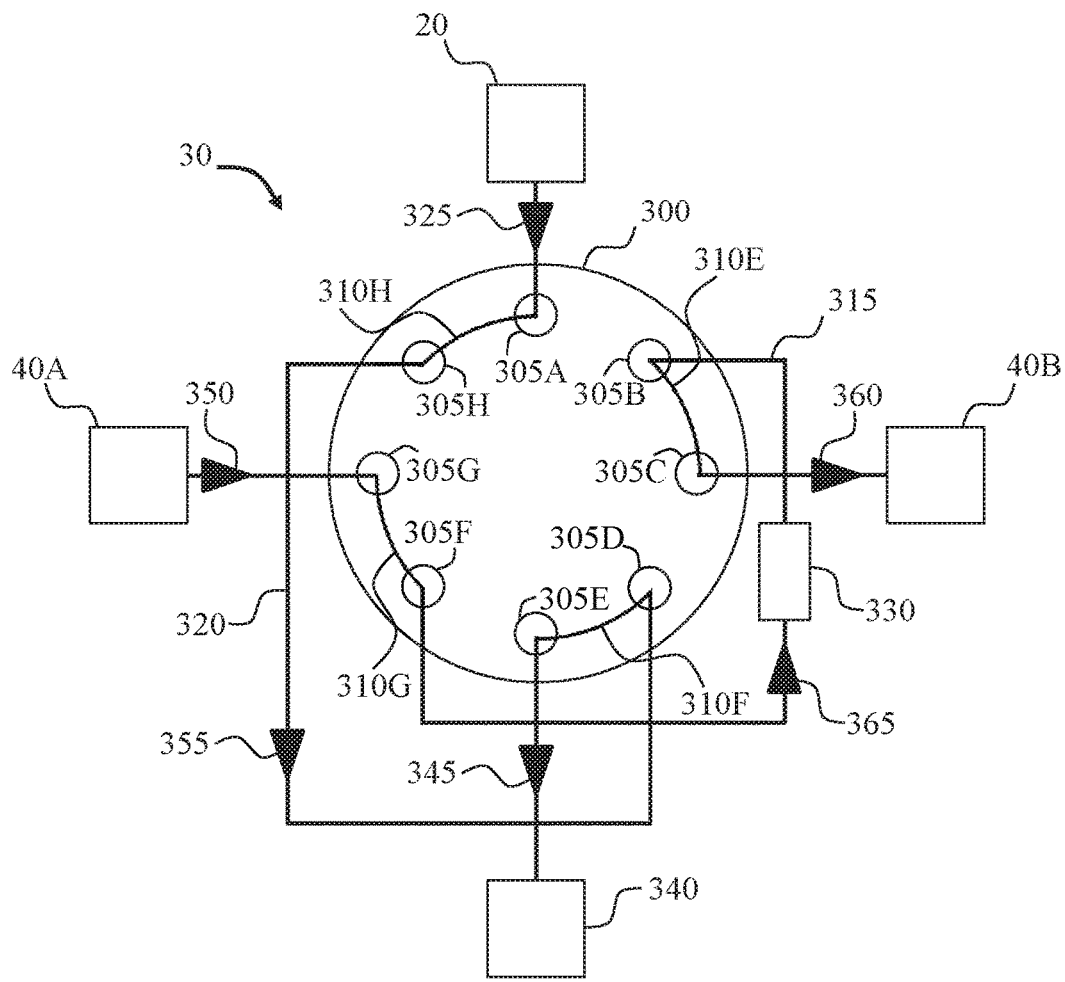

The schematic illustrated in FIG. 3B depicts the same configuration of the first fluidic routing unit as shown in FIG. 3A, except the plurality of channels 310A-310D of the routing mechanism 300 in FIG. 3A are now in a second of two of possible positions, namely, channels 310E-310H, as shown in FIG. 3B. The routing mechanism in FIG. 3B directs the first mobile phase from the first separation unit 20, in the direction indicated by the arrow 325, through the channel 310H to the sample loop 320. The sample loop 320 is connected to the routing mechanism 300 at port 305H and port 305D wherein the first mobile phase is directed to the downstream receptacle 340, in the direction indicated by the arrow 345, via channel 310F.

As depicted in FIG. 3B, the upstream subunit 40A of the second separation unit is connected to the routing mechanism 300 at port 305G. The second mobile phase is driven through the second separation unit 40A in the direction indicated by the arrow 350 and the routing mechanism 300 now directs the second mobile phase to the sample loop 315 by way of a channel 310G. The sample loop 315 is connected to the routing mechanism at port 305B and port 305F. The routing mechanism 300 directs the flow of the second mobile phase through the trapping column 330 in the direction indicated by the arrow 365. As compared to FIG. 3A, the routing mechanism 300 as shown in FIG. 3B directs the flow of the second mobile phase through the sample loop 315 in a direction that is opposite of the flow of the first mobile phase through the same sample loop 315 shown in FIG. 3A. This exemplified configuration of the routing mechanism 300 directs the flow of the mobile phases through the sample loop 315 in what is known in the art as a "countercurrent" manner.

Figure 3C:
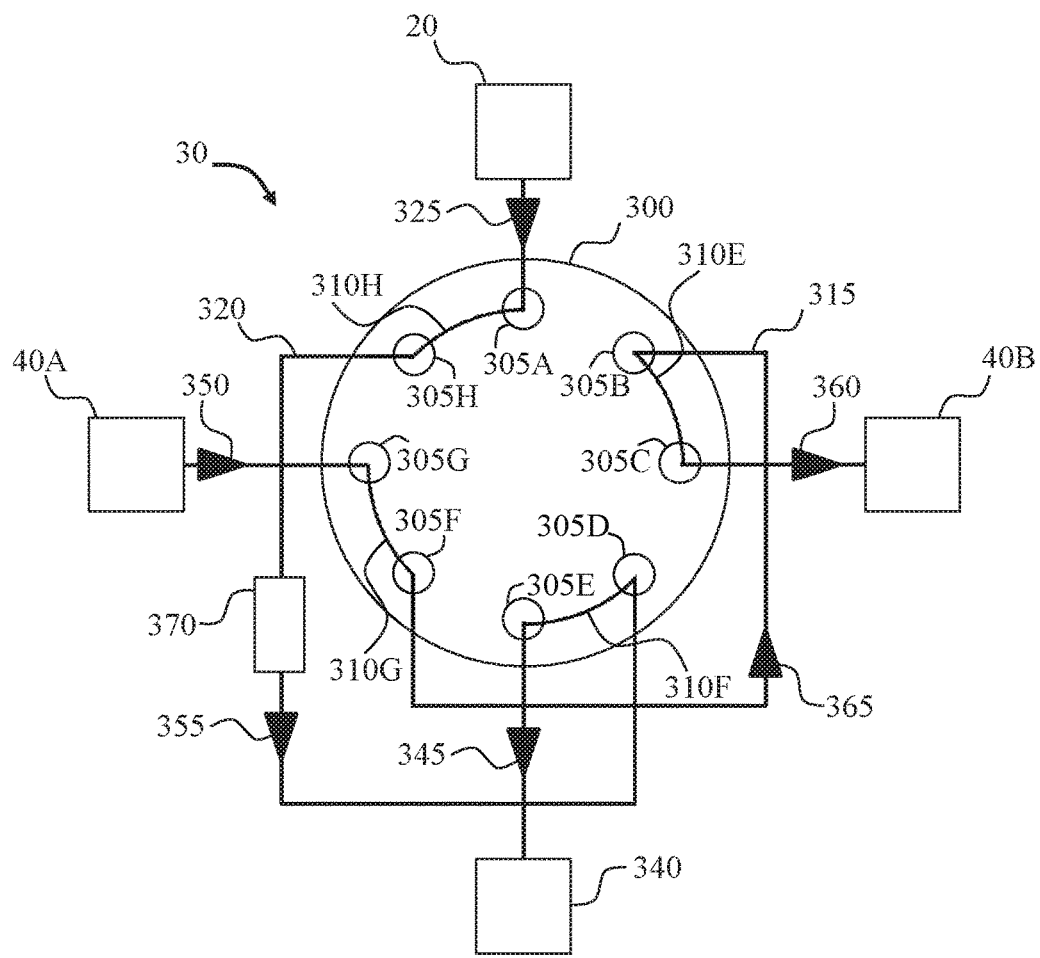
FIG. 3C and FIG. 3D are schematics of an exemplary first fluidic routing unit 30 comprising a trapping column 370, wherein the configuration of the first fluidic routing unit 30 is configured for co-current flow of the first mobile phase and second mobile phase through said trapping column 370.
Figure 3D:
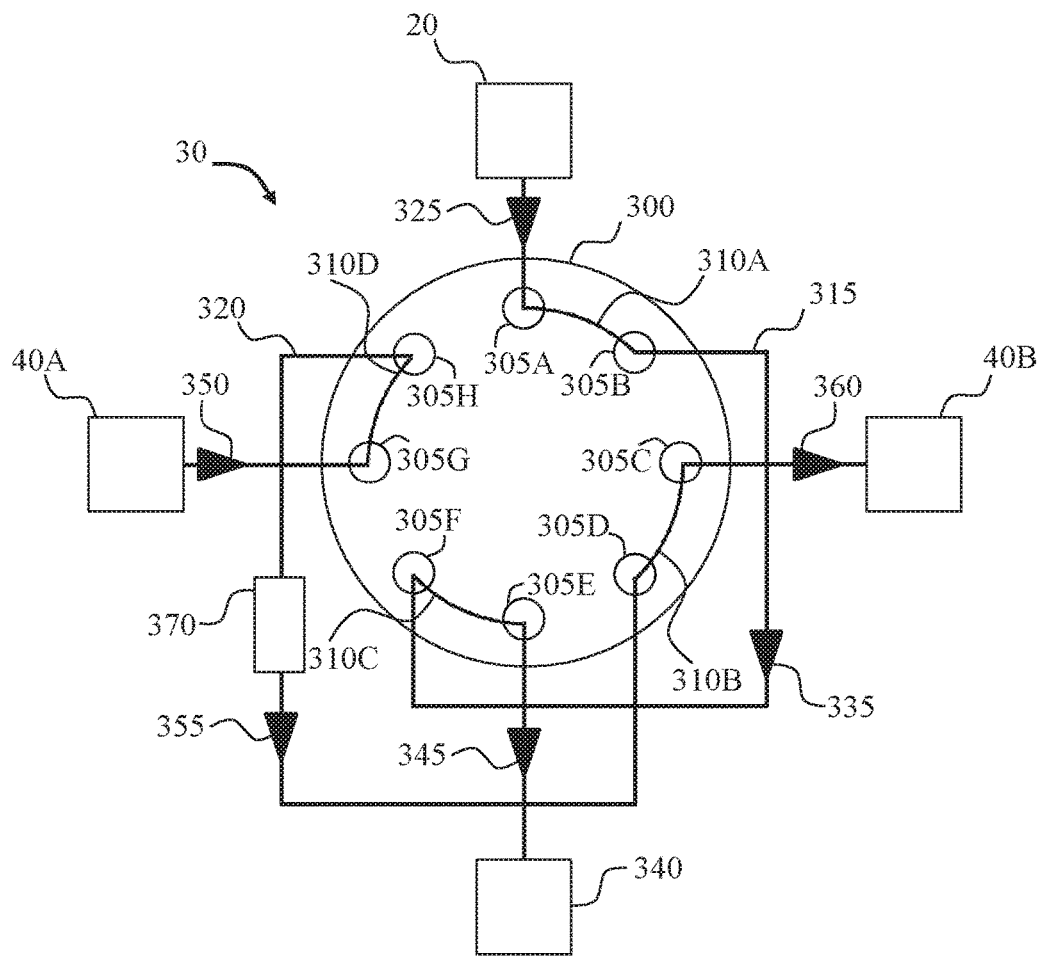

The exemplary schematics illustrated in FIG. 3C and FIG. 3D depict a similar configuration of the first fluidic routing unit shown in FIG. 3A and FIG. 3B, except, as shown in FIG. 3C and FIG. 3D, the trapping column 370 is located on sample loop 320. The routing mechanism 300 directs the flow of the first mobile phase through the sample loop 320 comprising the trapping column 370 in the direction indicated by the arrow 355 (FIG. 3C). In FIG. 3D, the plurality of channels 310A-310D of the routing mechanism 300 are in the second of two possible positions. The routing mechanism 300 directs the second mobile phase from upstream subunit 40A of the second separation unit through the sample loop 320 comprising the trapping column 370 and through the downstream portion of the second separation unit 40B in the direction indicated by the arrows 355 and 360. As exemplified in FIG. 3C and FIG. 3D flow of the first mobile phase and second mobile phase travel through the trapping column 370 in the same direction, known in the art as a "co-current" manner.

In the instance of a system using a 2-position/8-port switching valve (300) in the interface fluidic routing unit, the co-current/countercurrent configurations can be controlled by the placement of the trapping column (370) in sample loop 315 or 320. Alternatively, the co-current/countercurrent configurations can be changed by switching the port of connection for the upstream subunit 40A and the downstream subunit 40B of the second separation unit to the interface fluidic routing unit.

Figure 4A:
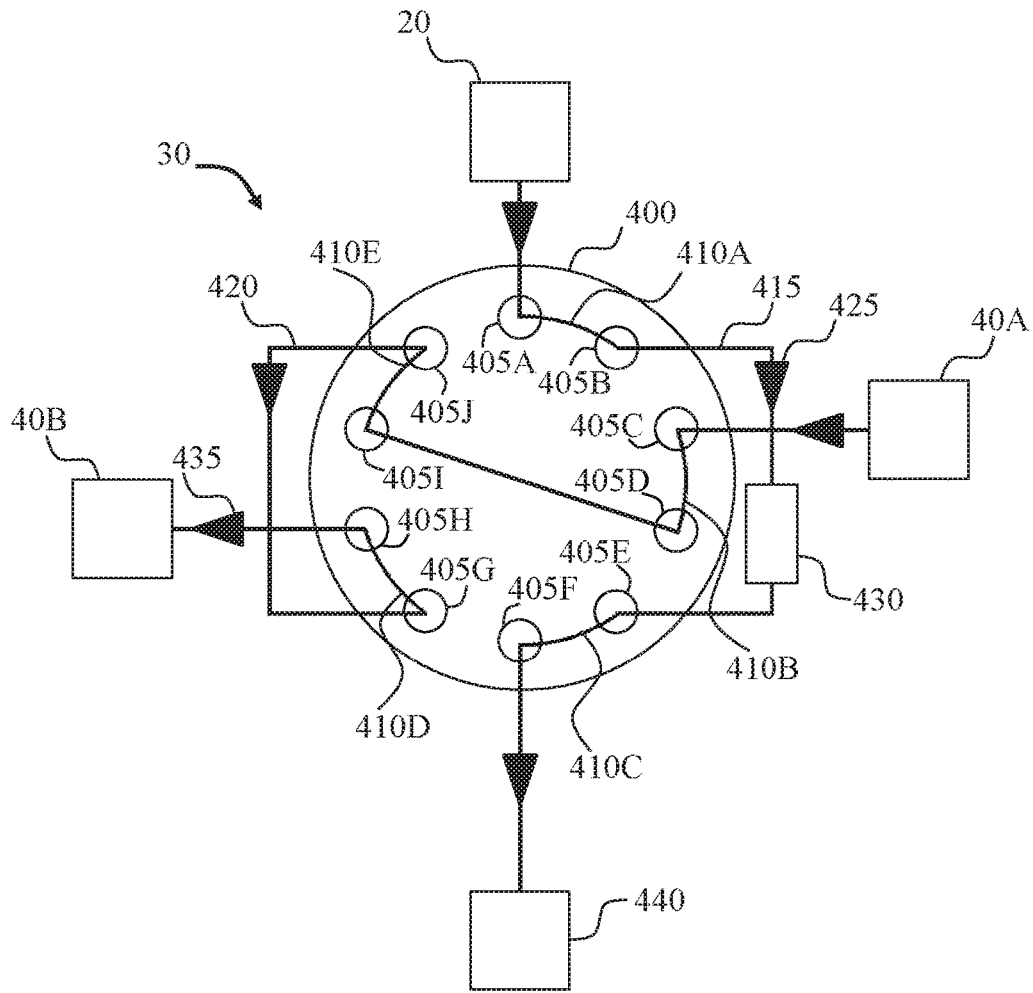
FIG. 4A and FIG. 4B are schematics of an exemplary first fluidic routing unit 30 comprising a trapping column 430, wherein the configuration of the first fluidic routing unit 30 is configured for co-current flow of the first mobile phase and second mobile phase through said trapping column 430.

FIG. 4A depicts a schematic of an exemplary first fluidic routing unit 30 interfaced with the first separation unit 20 and the second separation unit 40A and 40B. In this instance, the interface fluidic routing unit includes a routing mechanism 400, which in one variation is a 2-position/10-port switching valve, comprising a plurality of ports 405A-405J, a plurality of channels 410A-410E, and two sample loops 415 and 420. As shown in FIG. 4A, the plurality of channels 410A-410E are shown in the first of two possible configurations.

As exemplified in FIG. 4A, the first separation unit 20 is connected to the routing mechanism 400 at port 405A. The routing mechanism 400 directs the first mobile phase to one of the plurality of sample loops 415 by way of the channel 410A in the direction indicated by the arrow 425. The sample loop 415 is connected to the routing mechanism 400 at port 405B and port 405E. The sample loop 415 comprises a trapping column 430, said trapping column comprises a stationary phase.

The routing mechanism 400 directs the first mobile phase to a downstream receptacle 440 by way of a channel 410C. In some embodiments, the downstream receptacle 440 is a waste receptacle. In some embodiments, the downstream receptacle 440 is a fraction collector.

As depicted in FIG. 4A, the second separation unit 40 is connected to the routing mechanism 400 at port 405C. The routing mechanism 400 directs the second mobile phase to a sample loop 420 by way of two connected channels 410D and 410E. The sample loop 420 is connected to the routing mechanism 400 at port 405J and port 405G. The routing mechanism 400 is connected to the downstream subunit 40B of the second separation unit via port 405H. The routing mechanism 400 directs the second mobile phase through the downstream portion of the second fluidic routing unit 40B in the direction indicated by the arrow 435.

Figure 4B:
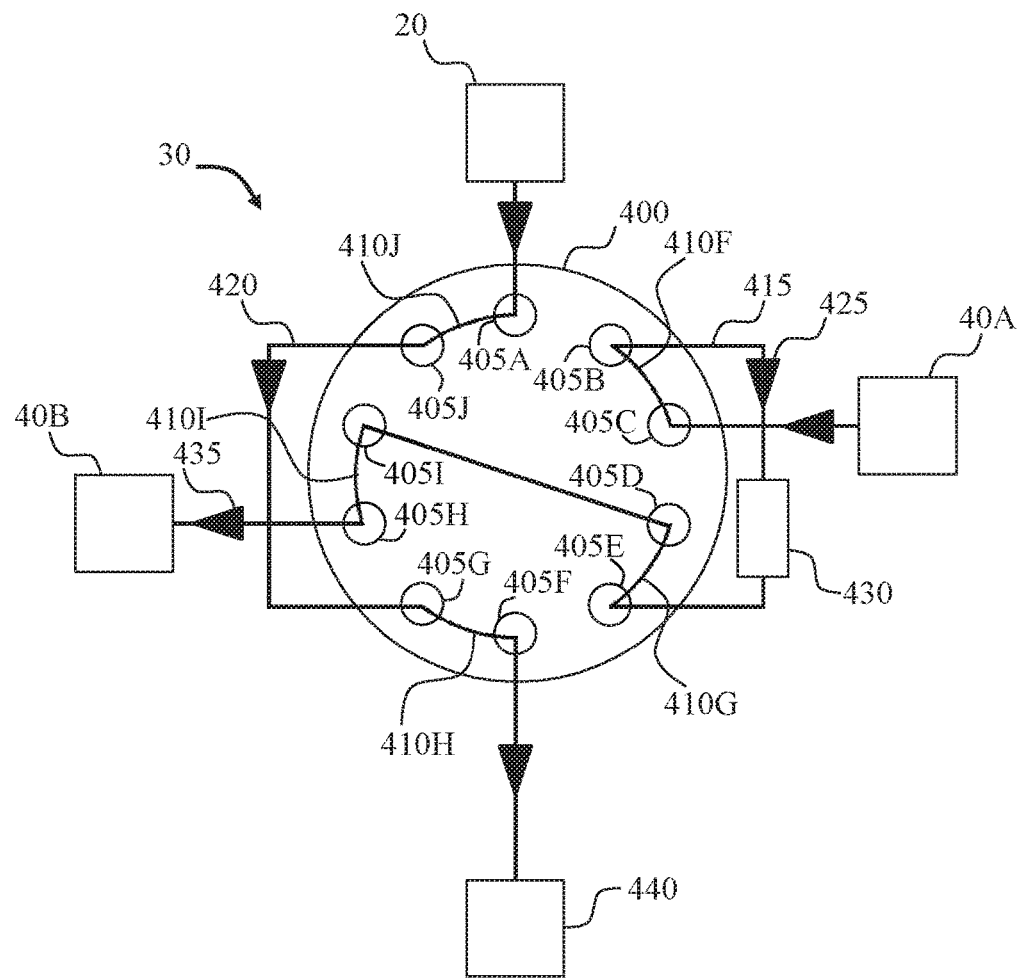

The schematic illustrated in FIG. 4B depicts the same configuration of the first fluidic routing unit as shown in FIG. 4A, except the plurality of channels 410A-410E of the routing mechanism 400 in FIG. 4A are now in a second of two of possible positions, namely, channels 410E-410J, as shown in FIG. 4B. As depicted in FIG. 4A and FIG. 4B, the routing mechanism 400 of the first separation unit 30 may be configured so that direction of the flow of the first mobile phase through a sample loop 415 (FIG. 4A) is in the same direction, indicated by the arrow 425, as the flow of the second mobile phase through the same sample loop 415 (FIG. 4B). This exemplified configuration of the routing mechanism 400 directs the flow of the mobile phases through the sample loop 415 in the co-current manner.

In the instance of a system using a 2-position/10-port switching valve (400) in the interface fluidic routing unit, both sample loops are configured in the co-current manner as depicted in FIG. 4A and FIG. 4B. However, both sample loops can be configured to countercurrent manner by switching the port of connection for the upstream subunit 40A and the downstream subunit 40B of the second separation unit to the interface fluidic routing unit.

Figure 5A:
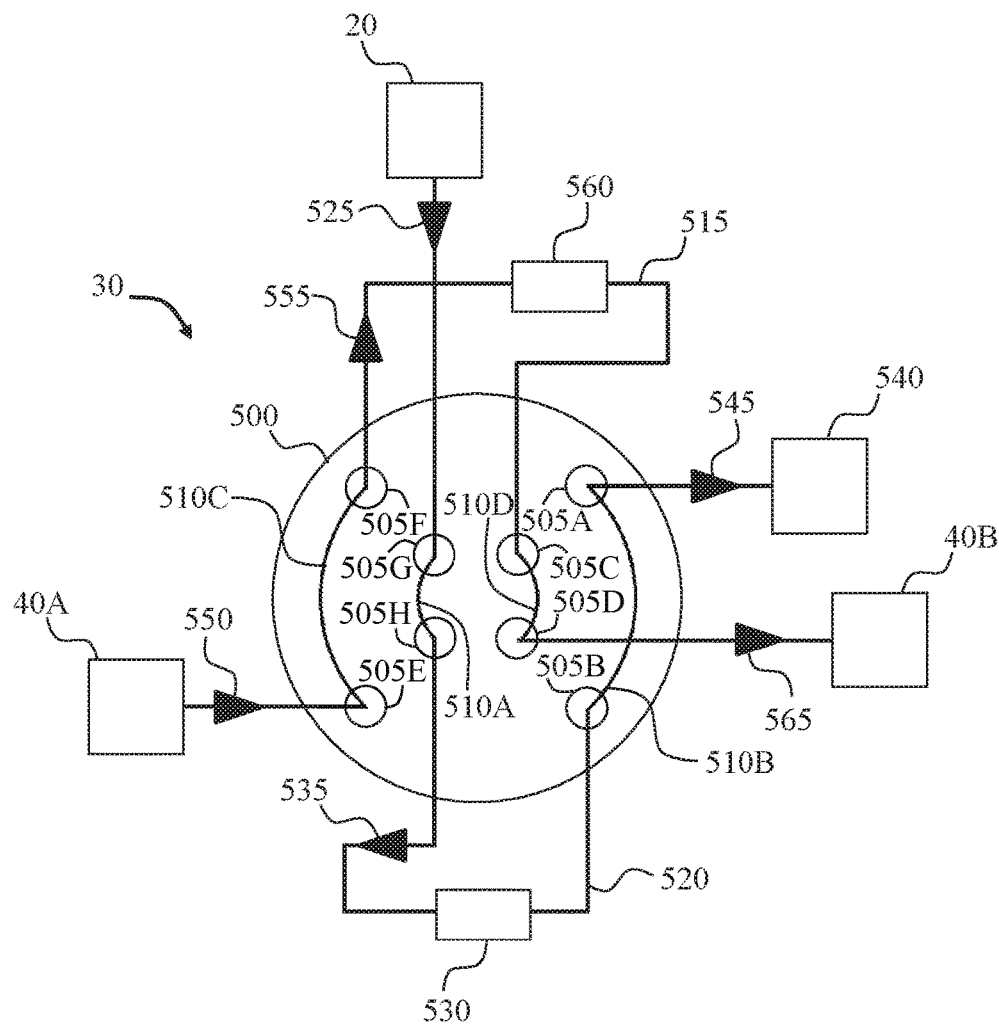
FIG. 5A and FIG. 5B are schematics of an exemplary first fluidic routing unit 30 comprising two trapping columns 530 and 560, wherein the configuration of the first fluidic routing unit 30 is configured for countercurrent flow of the first mobile phase and second mobile phase through each of the trapping columns 530 and 560.

FIG. 5A depicts a schematic of an exemplary first fluidic routing unit 30 interfaced with the first separation unit 20 and the second separation unit 40A and 40B. In this instance, the interface fluidic routing unit includes a routing mechanism 500, which in one variation is a 2-position/4-port duo valve, comprising a plurality of ports 505A-505H, a plurality of channels 510A-510D, and two sample loops, 515 and 520. As shown in FIG. 5A, the plurality of channels 510A-510D are shown in the first of two possible configurations.

As exemplified in FIG. 5A, the first separation unit 20 is connected to the routing mechanism 500 at port 505G. The first mobile phase is driven through the first separation unit 20 in the direction indicated by the arrow 525 and the routing mechanism 500 directs the first mobile phase through a sample loop 520 by way of a channel 510A. The sample loop 520 is connected to the routing mechanism 500 at port 505H and port 505B. The routing mechanism 500 directs the first mobile phase through the sample loop 520 in the direction indicated by the arrow 535. The sample loop 520 comprises a trapping column 530, said trapping column comprises a stationary phase.

The routing mechanism 500 directs the first mobile phase to a downstream receptacle 540, in the direction indicated by the arrow 545, by way of a channel 510B. In some embodiments, the downstream receptacle 540 is a waste receptacle. In some embodiments, the downstream receptacle 540 is a fraction collector.

As depicted in FIG. 5A, the upstream subunit 40A of the second separation unit is connected to the routing mechanism 500 at port 505E. The second mobile phase is driven through the second separation unit 40A in the direction indicated by the arrow 550 and the routing mechanism 500 directs the second mobile phase to a sample loop 515 by way of a channel 510C. The sample loop 515 is connected to the routing mechanism 500 at port 505F and port 505C, wherein the first mobile phase travels in the direction indicated by the arrow 555. The sample loop 515 comprises a trapping column 560, said trapping column comprises a stationary phase. The routing mechanism 500 is connected to the downstream subunit 40B of the second separation unit via port 505D. The routing mechanism 500 directs the second mobile phase through the downstream subunit 40B of the second separation unit in the direction indicated by the arrow 565.

In some embodiments, the trapping columns 530 and 560 comprise the same stationary phase. In some embodiments, the stationary phase may comprise a reversed-phase stationary phase. In some embodiments, the trapping columns 530 and 560 comprise the different stationary phase.

Figure 5B:
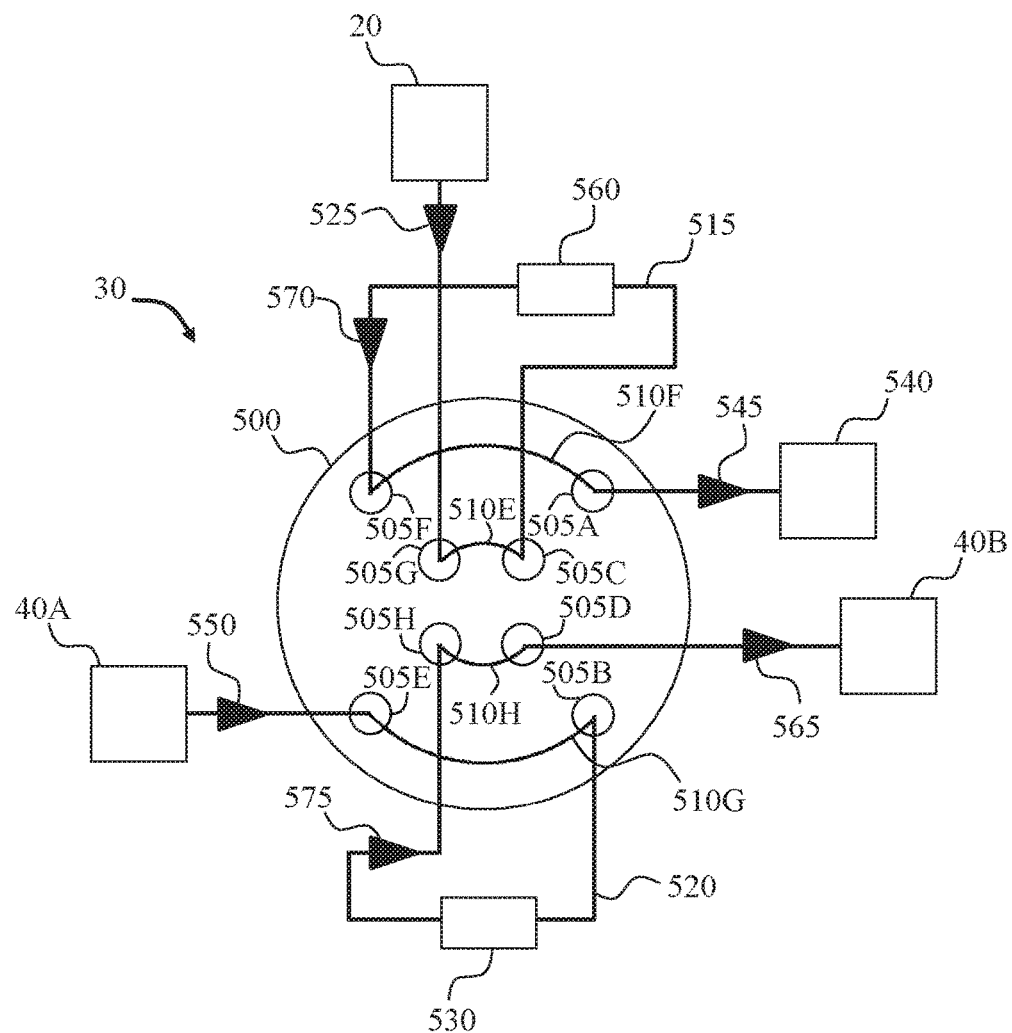

The schematic illustrated in FIG. 5B depicts the same configuration of the first fluidic routing unit as shown in FIG. 5A, except the plurality of channels 510A-510D of the routing mechanism 500 in FIG. 5A are now in a second of two possible positions, namely, channels 510E-510G, as shown in FIG. 5B. The routing mechanism 500 in FIG. 5B now directs the first mobile phase from the first separation unit 20, in the direction indicated by the arrow 525, through the channel 510E to the sample loop 515. The sample loop 515 is connected to the routing mechanism 500 at port 505C and port 505F wherein the first mobile phase is directed to the downstream receptacle 540, in the direction indicated by the arrow 545, via channel 510F. In FIG. 5B, the routing mechanism 500 directs the flow of the first mobile phase through the sample loop 515 in an opposite direction than that of the second mobile phase through the same sample loop 515 in FIG. 5A.

As depicted in FIG. 5B, the upstream subunit 40A of the second separation unit is connected to the routing mechanism 500 at port 505E. The second mobile phase is driven through the second separation unit 40A in the direction indicated by the arrow 550 and the routing mechanism 500 now directs the second mobile phase to the sample loop 520 by way of a channel 510G. The sample loop 520 is connected to the routing mechanism at port 505B and port 505H. The routing mechanism 500 directs the flow of the second mobile phase through the trapping column 530 in the direction indicated by the arrow 575. In FIG. 5B, the routing mechanism 500 directs the flow of the second mobile phase through the sample loop 520 in an opposite direction than that of the first mobile phase through the same sample loop 520 in FIG. 5A.

In the instance of a system using a 2-position/4-port duo valve (500) in the interface fluidic routing unit, both sample loops are configured in the countercurrent manner as depicted in FIG. 5A and FIG. 5B. However, if desirable, both sample loops can be configured in the co-current manner by switching the port of connection for the upstream subunit 40A and the downstream subunit 40B of the second separation unit to the interface fluidic routing unit.

In some embodiments, the first fluidic routing unit of the 2D RPLC×SFC system comprises at least three sample loops, and wherein at least one of the sample loops is in fluidic isolation from the first separation unit and the second separation unit. In such a system, one sample loop is in fluidic communication with the first separation unit, one sample loop is in fluidic communication with the second separation unit, and one or more sample loops are in fluidic isolation from the first separation unit and the second separation unit. In some embodiments, at least one of the sample loops comprises a trapping column, said trapping column comprises a stationary phase. In some embodiments, at least one sample loop which comprises a trapping column, said trapping column comprises a stationary phase, is in fluidic isolation from the first separation unit and the second separation unit. In some embodiments, the first fluidic routing unit comprises a plurality of trapping columns each positioned in a sample loop. In some embodiments, each of the trapping columns is loaded with the same stationary phase material. In other embodiments, the stationary phase material may be adapted for the particular analytes being retained, thus different stationary phase materials may be used for different fractions eluted from the first separation unit. In some embodiments, the stationary phase may comprise a reversed-phase stationary phase. In some embodiments, the reversed-phase stationary phase may comprise a carbon chain-bonded silica gel. In some embodiments, the carbon chain-bonded silica gel may comprise a carbon chain that is 18 carbons in length (i.e., C18-reversed-phase silica gel or C18 silica gel). In some embodiments, the carbon chain-bonded silica gel may comprise a carbon chain that is 8 carbons in length (i.e., C8-reversed-phase silica gel or C8 silica gel). In some embodiments, the carbon chain-bonded silica gel may comprise a carbon chain that is 4 carbons in length (i.e., C4-reversed-phase silica gel or C4 silica gel). In some embodiments, the reversed-phase stationary phase may comprise a carbon chain (such as a C-18, C-8 or C-4 carbon chain) bonded to a polymer core such as an organic polymer (e.g., polystyrene).

A system comprising an interface fluidic routing unit where one or more sample loops can be placed in fluidic isolation from the first separation unit and the second separation unit provides for a "peak parking" feature. When multiple fractions separated and eluted from the first dimension chromatography need to be further separated in the second dimension, the time interval between fractions eluted from the first separation unit may be insufficient for the first fraction to run through the second separation unit. While the second separation unit is in use for analyzing an earlier fraction, later fractions (or cuts) can be collected on a trapping column in additional loops and retained in fluidic isolation ("parked") until the second separation unit is ready for the analyzing the next fraction.

Figure 6A:
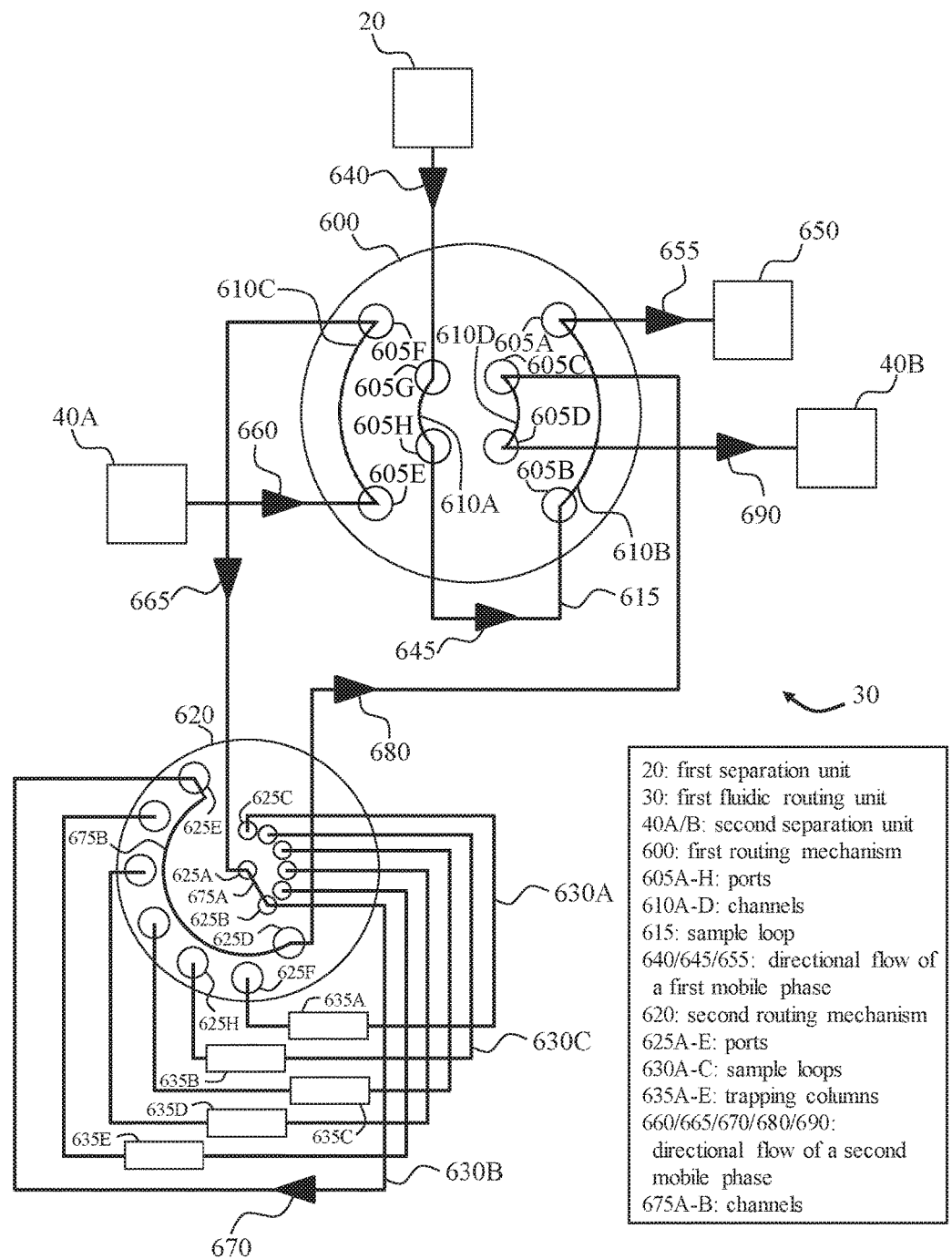
FIG. 6A, FIG. 6B, FIG. 6C and FIG. 6D are schematics of an exemplary first fluidic routing unit 30 comprising two routing mechanisms 600 and 620.

Referring to the drawings, FIG. 6A depicts a schematic of an exemplary first fluidic routing unit 30 interfaced with the first separation unit 20 and the second separation unit 40A and 40B. In this instance, the interface fluidic routing unit includes a first routing mechanism 600, which in one variation is a 2-position/4-port duo valve, comprising a plurality of ports 605A-605H, a plurality of channels 610A-610D, a sample loop 615, and second routing mechanism 620 comprising a plurality of ports, for example 625A-625E, a plurality of sample loops, for example, 630A-630C, a plurality of trapping columns, 635A-635E, and plurality of channels 675A and 675B. Sample loop 630B provides for a by-pass loop without a trapping column. As shown in FIG. 6A, the plurality of channels 610A-610D of the first routing mechanism 600 are shown in the first of two possible configurations.

As exemplified in FIG. 6A, the first separation unit 20 is connected to the routing mechanism 600 at port 605G. The first mobile phase is driven through the first separation unit 20 in the direction indicated by the arrow 640 and the routing mechanism 600 directs the first mobile phase through a sample loop 615 by way of a channel 610A. The sample loop 615 is connected to the first routing mechanism 600 at port 605H and port 605B. The first routing mechanism 600 directs the first mobile phase through the sample loop 615 in the direction indicated by the arrow 645. As shown in FIG. 6A, the routing mechanism 600 directs the first mobile phase to a downstream receptacle 650, in the direction indicated by the arrow 655, by way of a channel 610B. In some embodiments, the downstream receptacle 650 is a waste receptacle. In some embodiments, the downstream receptacle 650 is a fraction collector.

As depicted in FIG. 6A, the upstream subunit 40A of the second separation unit is connected to the routing mechanism 600 at port 605E. The second mobile phase is driven through the upstream subunit 40A of the second separation unit in the direction indicated by the arrow 660. The routing mechanism 600 directs the second mobile phase, in the direction indicated by the arrow 665, to a second routing mechanism 620 by way of channel 610C. The first routing mechanism 600 and second routing mechanism 620 are connected via port 605F and port 625A.

In FIG. 6A, the second routing mechanism 620 is configured to direct the second mobile phase through a sample loop 630B in the direction indicated by the arrow 670 via channel 675A. Sample loop 630B is connected to the second routing mechanism 620 via port 625B and port 625E, which is connected to port 625D via channel 675B. The second routing mechanism 620 and first routing mechanism 600 are connected via port 625F and port 605C. The second routing mechanism 620 directs the flow the second mobile phase back to the first routing mechanism 600 in the direction indicated by the arrow 680. The first routing mechanism 600 directs the flow of the second mobile phase through the downstream subunit 40B of the second separation unit via channel 610D in the direction indicated by the arrow 690.

FIG. 6A depicts a configuration where no trapping column is in fluidic communication with either the first separation unit or the second separation unit. For example, the system can be set to this configuration when no peak of interest is coming out of the first dimension column or being analyzed in the second dimension column. The system may also be set to this configuration when the columns in both separation units are in idle state or the columns are undergoing regeneration/equilibration. Each one of trapping columns 635A-635E is in fluidic isolation from the first and second separation unit.

Figure 6B:
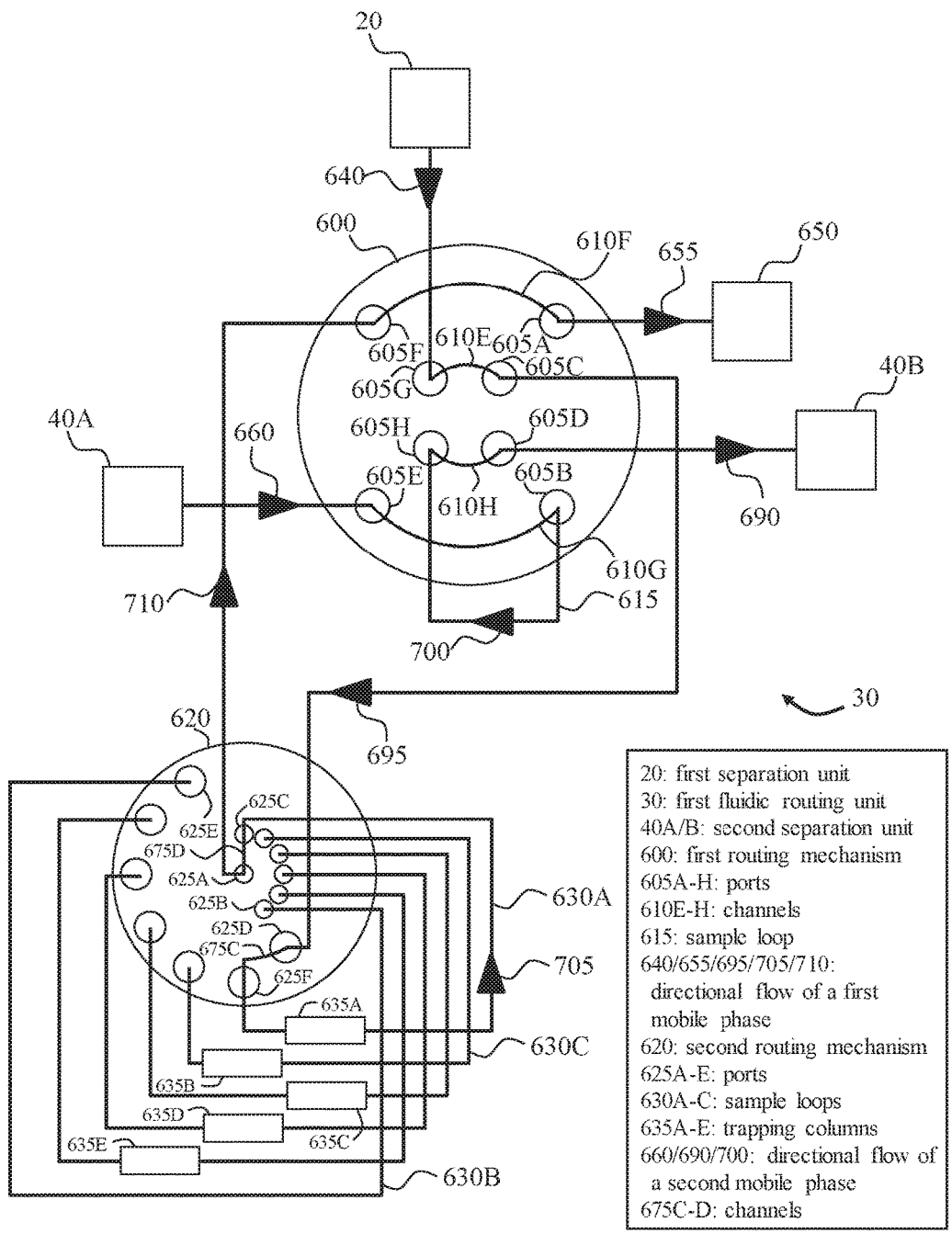

The schematic illustrated in FIG. 6B depicts the same configuration of the first fluidic routing unit as shown in FIG. 6A, except the plurality of channels 610A-610D of the first routing mechanism 600 in FIG. 6A are now in the second of two possible positions 610E-610H as shown in FIG. 6B. The routing mechanism 600 in FIG. 6B now directs the first mobile phase from the first separation unit 20, in the direction indicated by the arrow 640, through the channel 610E to the second routing mechanism 620. The first routing mechanism 600 and the second routing mechanism 620 are connected at port 605C and port 625F. Additionally, in FIG. 6B, the second routing mechanism 620 is now configured to direct the flow of the first mobile phase through the sample loop 630A in the direction indicated by the arrow 705. Sample loop 630A comprises a trapping column 635A. Sample loop 630A is connected to the second routing mechanism 620 via port 625F and port 625C. As depicted in FIG. 6B, the second routing mechanism 620 and first routing mechanism 600 are connected via port 625A and port 605F. The second routing mechanism 620 directs the flow the first mobile phase back to the first routing mechanism 600 in the direction indicated by the arrow 710. The first routing mechanism 600 directs the first mobile phase to a downstream receptacle 650, in the direction indicated by the arrow 655, by way of a channel 610F. In some embodiments, the downstream receptacle 650 is a waste receptacle. In some embodiments, the downstream receptacle 650 is a fraction collector. In some embodiments, a Flexcube (Agilent) may be used as part of the second routing mechanism.

In some embodiments, the configuration of the first fluidic routing unit 30 shown in FIG. 6B, may be used to direct a portion of the sample eluting from the first separation unit to be selectively retained on a trapping column, for example, 635A. In some embodiments, the trapping column may comprise a stationary phase. In some embodiments, the stationary phase may comprise a reversed-phase stationary phase. In some embodiments, the reversed-phase stationary phase may comprise a carbon chain-bonded silica gel (e.g., C18 silica gel, C8 silica gel and C4 silica gel). In some embodiments, the reversed-phase stationary phase may comprise a carbon chain (such as a C-18, C-8 or C-4 carbon chain) bonded to a polymer core such as an organic polymer (e.g., polystyrene).

Figure 6C:
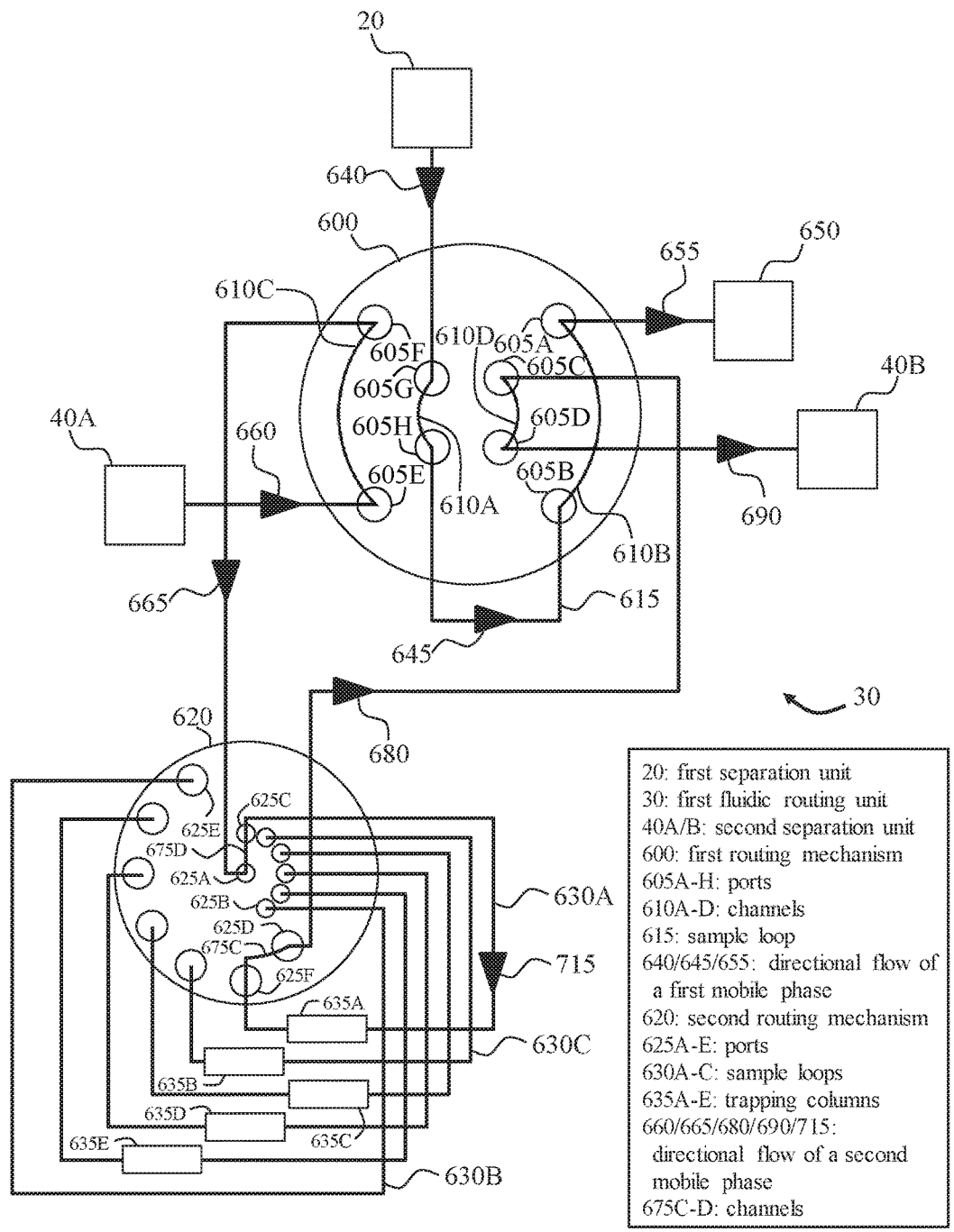
Figure 6D:
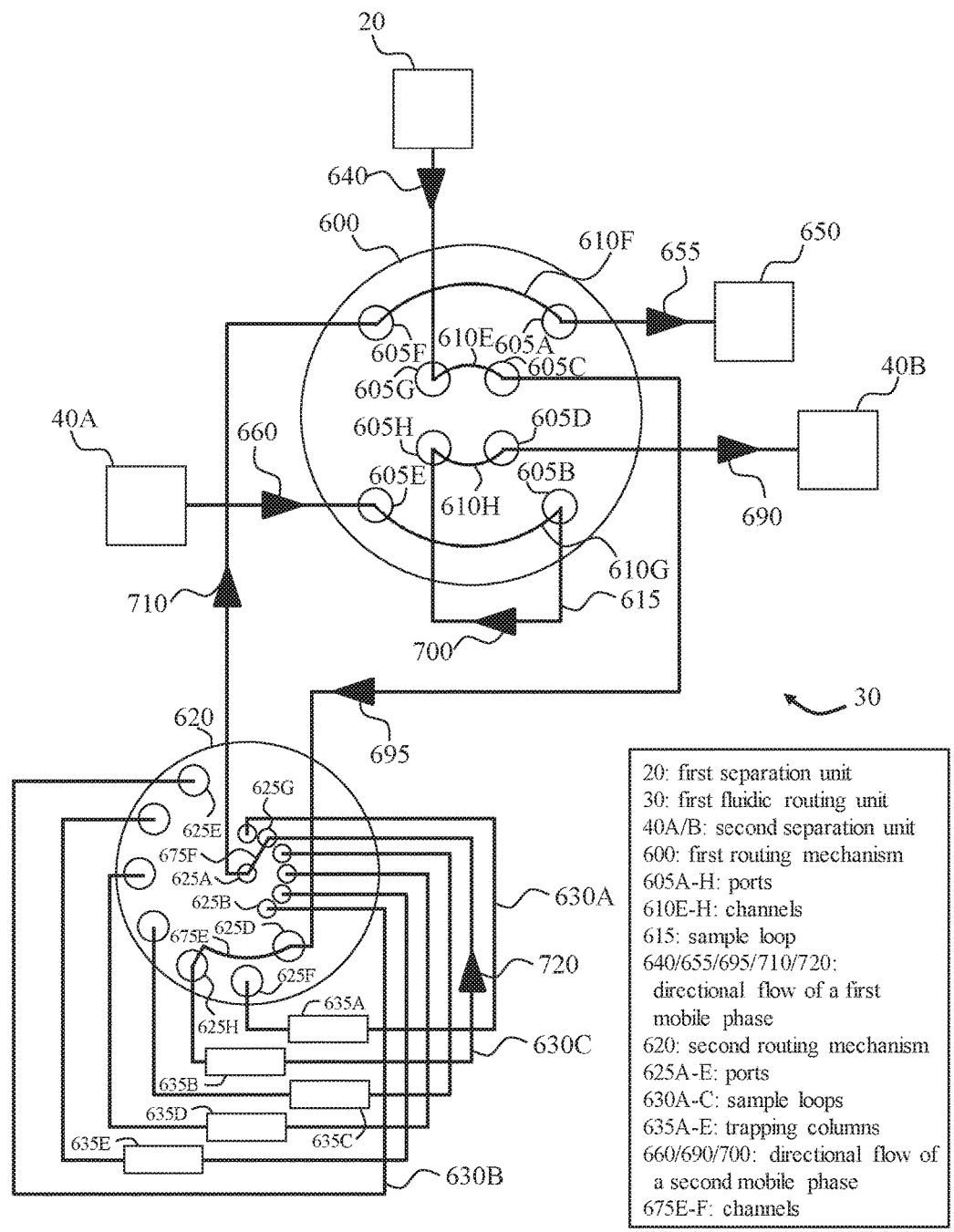

After a peak has been retained on a trapping column, for example, 635A, the routing mechanisms 600 and 620 can be switched or set to positions to allow elution and further analysis of the retained peak, for example as shown in FIG. 6C; or the routing mechanisms 600 and 620 can be switched or set to positions to allow parking of the peak retained on trapping column 635A and collection of another peak on a different trapping column, for example, 635B, as demonstrated in FIG. 6D.

The schematic illustrated in FIG. 6C depicts an exemplary configuration of the first fluidic routing unit 30 wherein the first routing mechanism 600 is configured to direct the flow of the first mobile phase to the downstream receptacle 650, as shown in FIG. 6A. As illustrated in FIG. 6C, the first mobile phase is driven through the first separation unit 20 in the direction indicated by the arrow 640 and the routing mechanism 600 directs the first mobile phase through a sample loop 615 by way of a channel 610A. The sample loop 615 is connected to the first routing mechanism 600 at port 605H and port 605B. The first routing mechanism 600 directs the first mobile phase through the sample loop 615 in the direction indicated by the arrow 645. As shown in FIG. 6A, the routing mechanism 600 directs the first mobile phase to a downstream receptacle 650, in the direction indicated by the arrow 655, by way of a channel 610B. In some embodiments, the downstream receptacle 650 is a waste receptacle. In some embodiments, the downstream receptacle 650 is a fraction collector.

In FIG. 6C, the first routing mechanism 600 directs the flow of the second mobile phase to the second fluidic routing mechanism 620 in the direction indicated by the arrow 665. The second routing mechanism 620 is configured to direct the second mobile phase to sample loop 635A via channel 675D in the direction indicated by the arrow 715. Sample loop 635A is connected to the second fluidic routing mechanism via port 625C and port 625F. The second fluidic routing mechanism 620 is configured to direct the flow of the second mobile phase to the first fluidic routing mechanism 600 via channel 675C in the direction indicated by the arrow 680. The second fluidic routing mechanism and the first fluidic routing mechanism are connected via port 625D and 605C and the second mobile phase is directed to the downstream portion 40B of the second separation unit via channel 610D in the direction indicated by the arrow 690.

The schematic illustrated in FIG. 6D depicts the same configuration of the first fluidic routing mechanism 600 and the second fluidic routing mechanism 620 as shown in FIG. 6B, except in FIG. 6D, the second fluidic routing mechanism now directs the flow of the first mobile phase to sample loop 630C in the direction indicated by the arrow 720. Sample loop 630C is connected to the second fluidic routing mechanism via port 625G and port 625H. Channel 675F connects port 625A and port 625G. Channel 675E connects port 625D and port 625H. As depicted in FIG. 6B, sample loop 630C comprises a trapping column 635B, which may comprise a stationary phase, such as a stationary phase as described herein.

As exemplified in FIG. 6D, the portion of the sample eluted from the first separation unit and selectively retained on the trapping column 635A is now in isolation from both the first separation unit 20 and second separation unit 40A and 40B.

In some embodiments, the plurality of trapping columns 635A-635E, such as shown in FIG. 6A-FIG. 6D, may comprise the same stationary phase. In some embodiments, the stationary phase may comprise a reversed-phase stationary phase. In some embodiments, at least one of the plurality of trapping columns 635A-635E, such as shown in FIG. 6A-FIG. 6D, may comprise the same stationary phase as the stationary phase material used in the first dimension RPLC column. In some embodiments, the stationary phase may comprise a reversed-phase stationary phase. In some embodiments, the reversed-phase stationary phase may comprise a carbon chain-bonded silica gel. In some embodiments, the carbon chain-bonded silica gel may comprise a carbon chain that is 18 carbons in length (i.e., C18-reversed-phase silica gel). In some embodiments, the carbon chain-bonded silica gel may comprise a carbon chain that is 8 carbons in length (i.e., C8-reversed-phase silica gel). In some embodiments, the carbon chain-bonded silica gel may comprise a carbon chain that is 4 carbons in length (i.e., C4-reversed-phase silica gel). In some embodiments, the reversed-phase stationary phase may comprise a hydrocarbon chain (e.g., a C-18, C-8 or C-4 chain) bonded to a polymer core such as an organic polymer (e.g., polystyrene).

2D chromatography can be performed in heart-cutting, pseudo-comprehensive or comprehensive modes. Heart-cutting provides the characterization of a selected region of the chromatogram, while the comprehensive mode provides the characterization of the entire chromatogram. The pseudo-comprehensive mode provides comprehensive separation of selected regions of the chromatogram. See Venkatramani, C. J. et al., *J. Sep. Sci.* 2014, 22, in-press. The interface in the 2D RPLC×SFC system, i.e., the first fluidic routing unit, can be adapted to perform in any one or more of the heart-cutting, pseudo-comprehensive and comprehensive modes. For example, a 2D RPLC×SFC system having any of the interface fluidic routing unit as depicted in FIGS. 3-6 herein may be used in the heart-cutting mode. A system having an interface fluidic routing unit comprising two sample loops (each having a trapping column) as depicted in FIGS. 5A and 5B may be used in pseudo-comprehensive mode if a long RPLC column coupled with a slow flow rate of the mobile phase in the first dimension would allow a complete run of one fraction in the second dimension separation while another fraction is collected in the second sample loop. A system having an interface fluidic routing unit with the sample parking feature as depicted in FIGS. 6A-6D can be used in comprehensive mode or pseudo-comprehensive mode as multiple fractions from the first dimension separation can be collected and retained for subsequent analysis in the second dimension when the second separation unit is available.

The separation criteria in the second dimension may depend on the nature of the analytes to be separated. Different stationary phase materials may be required for the SFC column in order to provide optimal separation for the various analytes eluted from the first dimension RPLC column. Thus, provided is a 2D RPLC×SFC chromatography system described herein, wherein the second separation unit comprises an array of SFC columns, wherein the SFC columns in the array are arranged in a parallel configuration; and a second fluidic routing unit for directing flow of the second mobile phase to a desired (or pre-identified) SFC column in the array. In some embodiments, the second separation unit further comprises a focus column located upstream of each SFC column in the array of SFC columns. In some embodiments, the focus column comprises a stationary phase. In some embodiments, the stationary phase may comprise a reversed-phase stationary phase. In some embodiments, the reversed-phase stationary phase may comprise a carbon chain-bonded silica gel. In some embodiments, the carbon chain-bonded silica gel may comprise a carbon chain that is 18 carbons in length (i.e., C18-reversed-phase silica gel). In some embodiments, the carbon chain-bonded silica gel may comprise a carbon chain that is 8 carbons in length (i.e., C8-reversed-phase silica gel). In some embodiments, the carbon chain-bonded silica gel may comprise a carbon chain that is 4 carbons in length (i.e., C4-reversed-phase silica gel). In some embodiments, the reversed-phase stationary phase may comprise a hydrocarbon chain (e.g., a C-18, C-8 or C-4 chain) bonded to a polymer core such as an organic polymer (e.g., polystyrene).

Figure 7A:
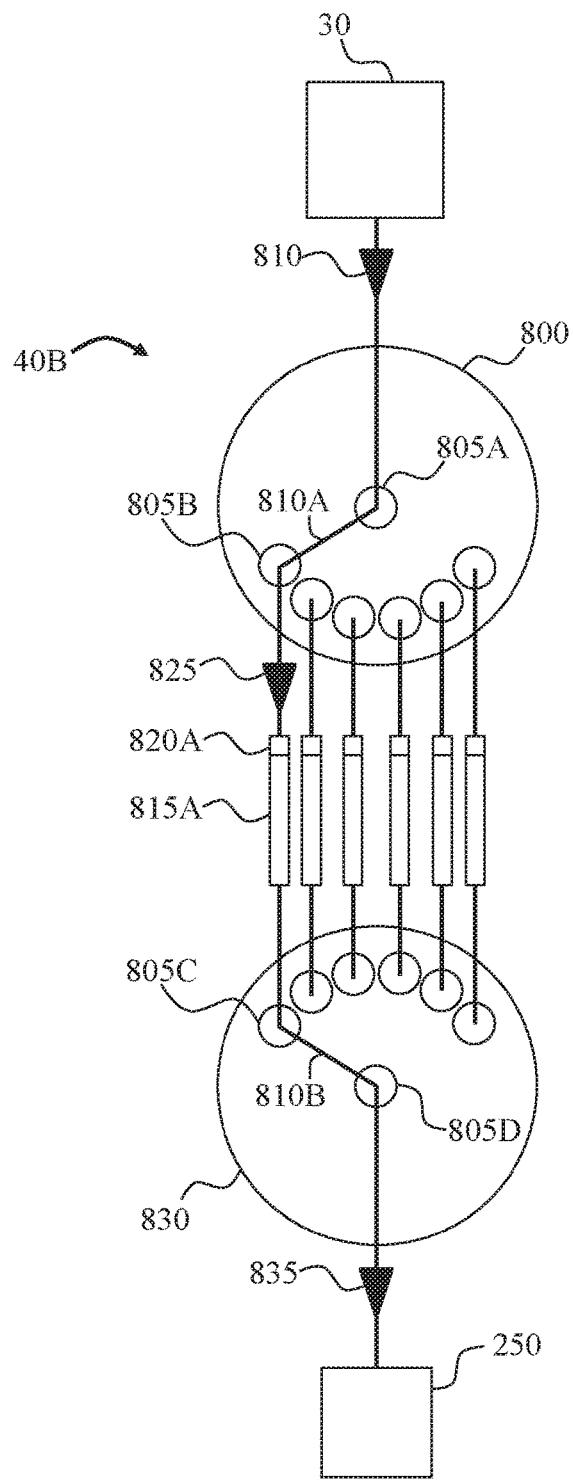
FIG. 7A and FIG. 7B are schematics of an exemplary downstream subunit of the second separation unit 40B comprising an array of SFC columns.
Figure 7B:
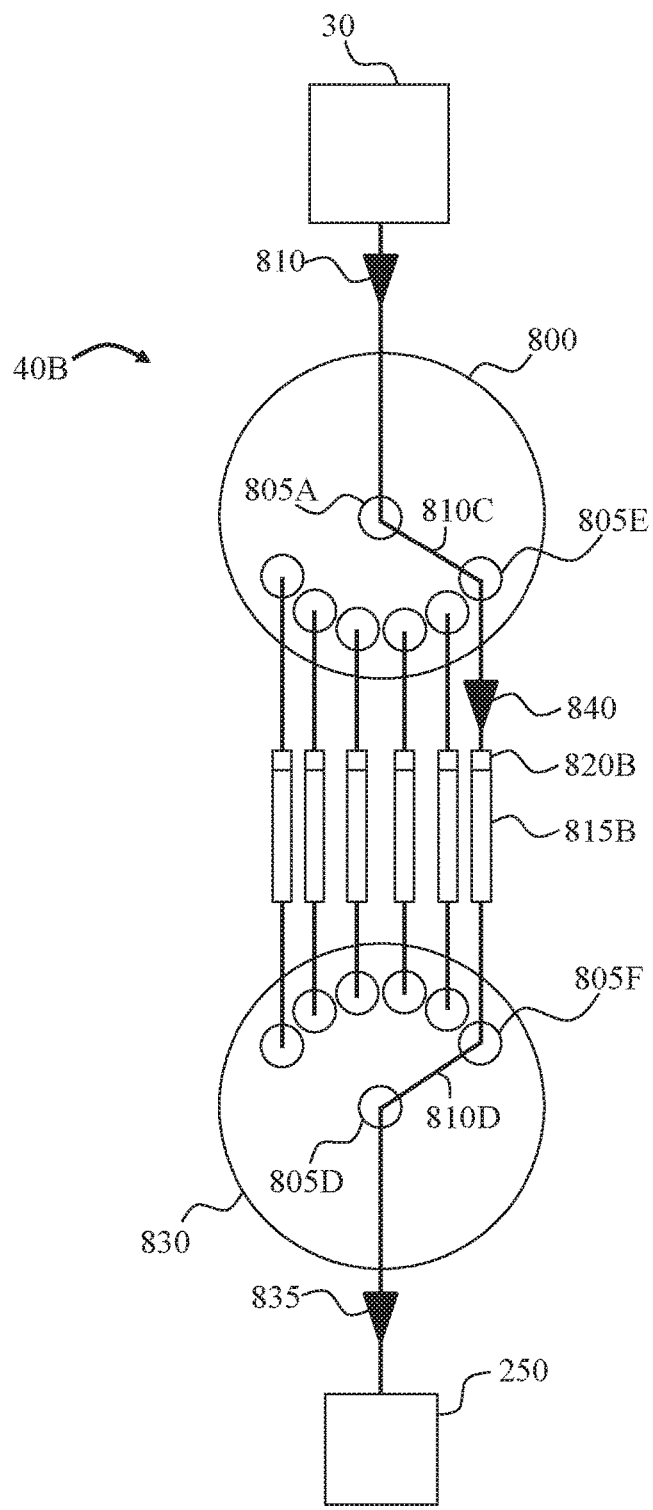

Referring to the drawings, FIG. 7A and FIG. 7B are schematics of an exemplary downstream subunit 40B of the second separation unit comprising a second fluidic routing unit 800 and an array of SFC columns. The first fluidic routing unit 30 is connected to the second fluidic routing unit 800 at port 805A. The first fluidic routing unit 30 directs the second mobile phase to the second routing unit 800 in the direction indicated by the arrow 810. The second routing unit 800 comprises a plurality of ports, such as port 805A and port 805B, and a plurality of channels, such as channel 810A. As depicted in FIG. 7A, the second fluidic routing unit 800, directs the second mobile phase to a desired (or pre-identified) SFC column 815A in the direction indicated by the arrow 825. Optionally, a focus column 820A is located upstream of the SFC column 815A.

In some embodiments, a routing mechanism 830 is optionally located downstream of the SFC column. As depicted in FIG. 7A, the routing mechanism 830 directs the second mobile phase to a detector 250 via channel 810B in the direction indicated by the arrow 835.

FIG. 7B depicts the same SFC column array as illustrated in FIG. 7A, but in FIG. 7B the second fluidic routing unit 800 is configured to direct the second mobile phase from the first fluidic routing unit to a second desired SFC chromatography column 815B. As depicted in FIG. 7B, the second desired SFC chromatography column is connected to the second fluidic routing unit 800 and the routing mechanism 830 via port 805E and port 805F. The second fluidic routing unit 800 directs the second mobile phase in the direction indicated by the arrow 840. Optionally, a focus column 820B is located upstream of the SFC column 815B.

In some embodiments, the SFC column array comprises a plurality of SFC columns wherein an individual SFC column, such as 815A, may comprise the same stationary phase as at least one other individual SFC column in the array, such as 815B. In some embodiments, the SFC column array comprises a plurality of SFC columns wherein an individual SFC column, such as 815A, may comprise a different stationary phase from all other individual SFC column in the array, such as 815B. In some embodiments, the stationary phase may comprise a normal phase stationary phase. In some embodiments, the normal phase stationary phase is silica. In some embodiments, the normal phase stationary phase is silica modified with propylcyano functional groups. In some embodiments, the normal phase stationary phase is silica modified with aminopropyl functional groups. In some embodiments, the normal phase stationary phase is silica modified with ethyl pyridine functional groups. In some embodiments, the normal phase stationary phase is silica modified with sulfonic acid and/or phenyl functional groups. In some embodiments, the normal phase stationary phase is silica modified with 1,2-dihydroxypropyl propyl ether functional groups. In some embodiments, the normal phase stationary phase is a polymer, such as an organic polymer (e.g., polystyrene), modified with a functional group (e.g., a cyanopropyl, aminopropyl, ethyl pyridine, sulfonic acid, phenyl, or 1,2-dihydroxypropyl propyl ether functional group).

In some embodiments, the SFC column array comprises a plurality of focus columns wherein an individual focus column, such as 820A, may comprise the same stationary phase as at least one other individual focus column in the array, such as 820B. In some embodiments, the SFC column array comprises a plurality of focus columns wherein an individual focus column, such as 820A, may comprise a different stationary phase from all other individual focus column in the array, such as 820B.

Figure 8A:
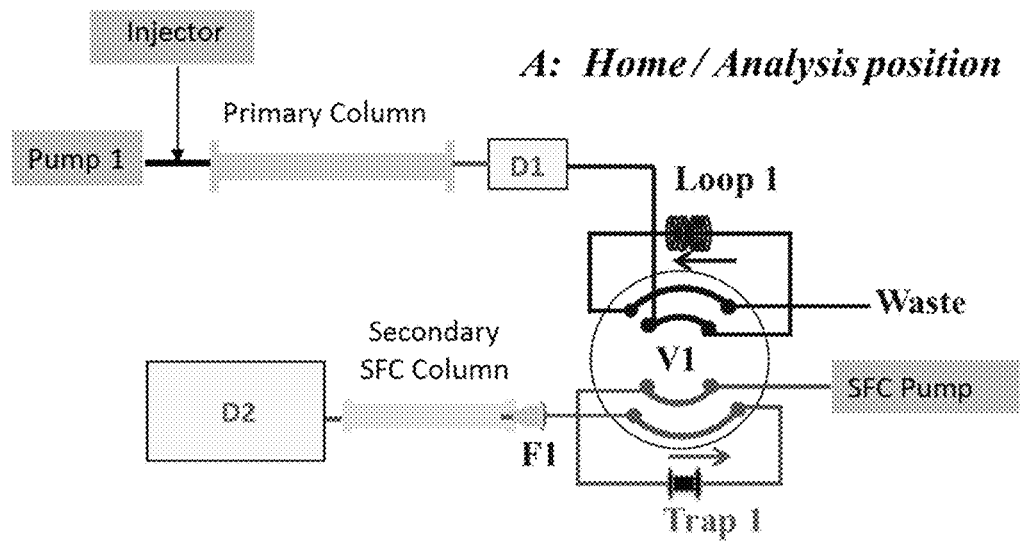
FIG. 8A and FIG. 8B depict the home/analysis position and the trapping position, respectively, of an exemplary 2D RPLC×SFC system with one trapping column (co-current flow).
Figure 8B:
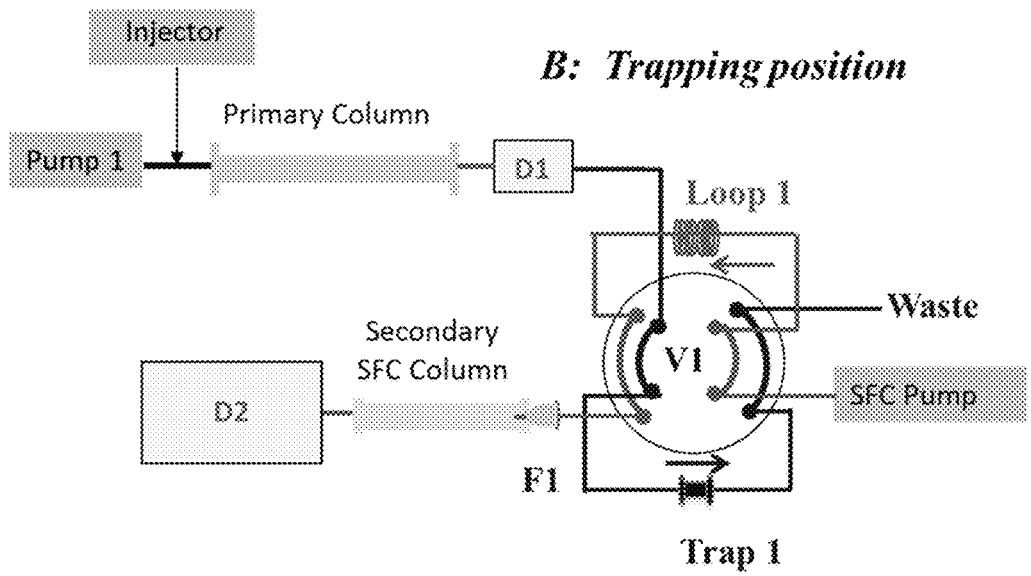

FIG. 8A and FIG. 8B depict schematics of an exemplary 2D LC-SFC system with an interface involving an electronically controlled, 2-position/4-port duo valve V1 and trapping column Trap 1. The mobile phase from the pump 1 flows through the injector to the reversed phase primary column. The eluent post detection D1 flows to the sampling valve V1. In the home/analysis position, the primary column eluent flows through the sampling loop Loop 1 exiting to waste. The mobile phase from the SFC pump flows through trapping column Trap 1 to the SFC column (FIG. 8A). This conditions the trapping column Trap 1 and SFC column. There is an uninterrupted flow of mobile phase through primary and secondary columns. When components of interest elute from the primary column, the valve V1 is switched (trapping position) transferring the primary column eluent to the trapping column Trap 1 (FIG. 8B). Switching the valve V1 back to home/analysis position flushes the sample components from trapping column T1 to the SFC column. The SFC column separation is monitored using UV detector D2 and/or a mass spectrometer. Interchanging positions of SFC pump and column in the valve V1 will result in countercurrent flow during valve switching.

In 2D chromatography involving repetitive gradients in secondary dimension, the frequency of transferring (sampling) the primary column eluent into the secondary column depends on the resolving speed of secondary column including the re-equilibration time. In 2D LC-SFC, the secondary dimension separation lasts about 2-3 minutes limiting the frequency of transferring the primary column eluent to the secondary column. If multiple analyte fractions (e.g., diastereomeric pairs in a sample containing a mixture of stereoisomers) elute from the primary column within 2-3 minutes, the 2D LC-SFC interface with a single trapping column shown in FIG. 8A and FIG. 8B may not be practical. Slowing the primary column flow rate and gradient to make-up for the sampling needs of secondary column speed is an option. However, this will result in poor peak shape and hence preclude simultaneous achiral/chiral analysis. This will require an interface with multiple trapping columns to meet the sampling needs of the secondary column.

Figure 9:
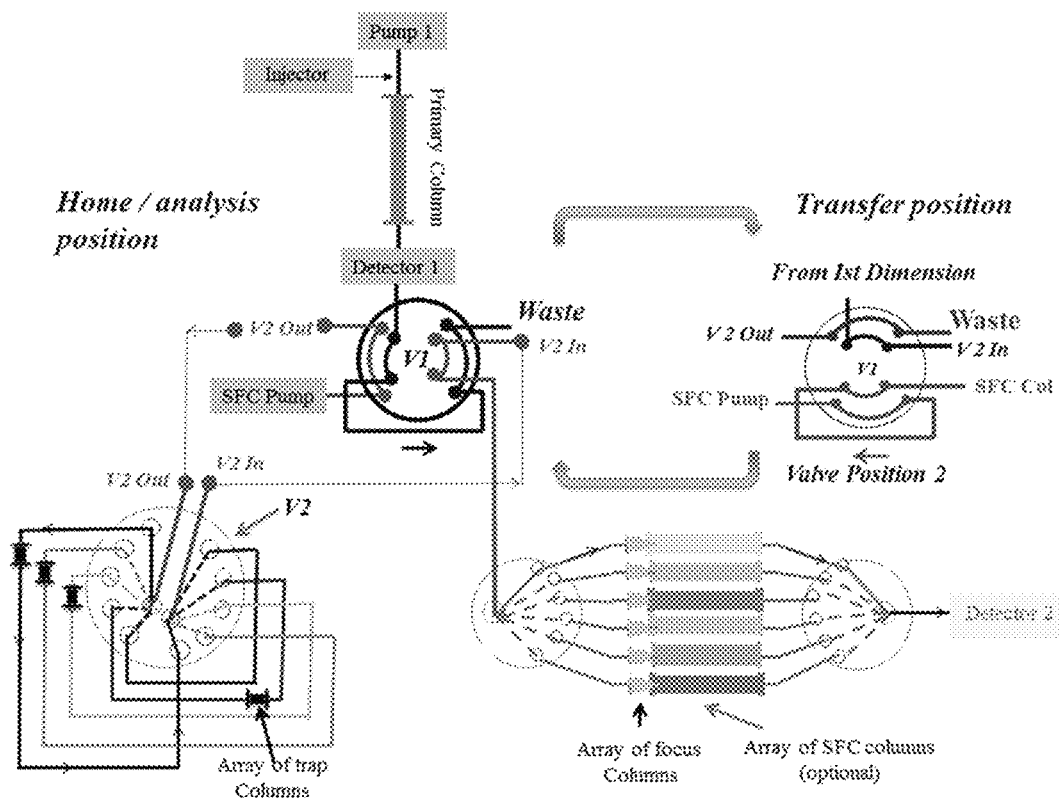
FIG. 9 shows a schematic diagram of 2D RPLC-SFC using an array of trapping columns, focusing columns, and secondary SFC columns.

FIG. 9 shows schematics of an exemplary 2D LC-SFC system with an interface using an array of trapping columns and secondary SFC columns. This configuration is used for analyzing multiple sections of the chromatogram. In the home/analysis position shown in FIG. 9, the eluent from the primary column post detection flows through a fully automated, 2-position/4-port duo valve V1 exciting to waste. The SFC mobile phase flows as follows: SFC pump through valve V1, to the parking deck valve V2, back to valve V1, and then to the SFC column(s). In valve V2, the SFC mobile phase flows either through by-pass tubing or an array of trapping columns. This conditions the trapping and SFC column(s). There is an uninterrupted flow of mobile phase through primary and secondary columns. When components of interest elute from the primary column, valve V1 is switched (home to transfer) transferring the primary column eluent to parking deck valve V2 (Out). By switching the parking deck valve V2 back and forth between the by-pass mode and trapping position, components are transferred to different trapping columns. Following the transfer of the primary column eluent, valve V1 is switched to home position diverting the primary column eluent to waste. This reverses the flow of mobile phase coming into valve V2 (V2-Out to V2-In). The direction of SFC flow in the parking deck valve V2 is reversed. Components retained in the trapping columns are subsequently back-flushed into a SFC column or an array of SFC columns for further separation depending upon the application. An array of SFC columns provides additional flexibility to the system as it might not be practical to resolve different components on a single chiral stationary phase. The secondary column separation is monitored using a UV or MS detector. The automated interface is the key component of the 2D LC-SFC system enabling simultaneous achiral, chiral analysis of sample in a single chromatographic run.

It is intended and understood that, in the 2D chromatograph system, each and every variation of the first separation unit described herein may be combined with each and every variation of the second separation unit described herein, and/or each and every combination of the first fluidic routing unit described herein, as if each and every combination is individually described. For example, in some embodiments, provided is a 2D chromatograph system comprising:
  (i) a first separation unit comprising:
    a) a first pump assembly for driving a first mobile phase through the first separation unit,
    b) a sample injector for introducing a sample to the first separation unit;
    c) a reversed-phase liquid chromatography (RPLC) column; and
    d) a first detector;
  (ii) a second separation unit comprising:
    a) a second pump assembly for driving a second mobile phase through the second separation unit,
    b) a supercritical fluid chromatography (SFC) column; and
    c) a second detector; and,
  (iii) a first fluidic routing unit comprising a plurality of sample loops, said first fluidic routing unit is connected to the first separation unit and the second separation unit, wherein at least one of the plurality of sample loops comprises a trapping column, said trapping column comprising a stationary phase; and
  wherein the chromatography system is configured for first separating the sample in the first separation unit and subsequently introducing at least a portion of the sample eluted from the RPLC column to the second separation unit.

In some embodiments, provided is a 2D chromatograph system comprising:
  (i) a first separation unit comprising:
    a) a first pump assembly for driving a first mobile phase through the first separation unit,
    b) a sample injector for introducing a sample to the first separation unit;
    c) a reversed-phase liquid chromatography (RPLC) column; and
    d) a first detector;
  (ii) a second separation unit comprising:
    a) a second pump assembly for driving a second mobile phase through the second separation unit,
    b) a supercritical fluid chromatography (SFC) column; and
    c) a second detector;
  (iii) a first fluidic routing unit comprising two sample loops, said first fluidic routing unit is connected to the first separation unit and the second separation unit, wherein one of the sample loops is in fluidic communication with the first separation unit, and the other one of the sample loops is in fluidic communication with the second separation unit;
    and wherein at least one of the of sample loops comprises a trapping column, said trapping column comprising a C-18 stationary phase (e.g., C-18 silica); and,
  (iv) at least one control device operably connected to one or more of:
    a) the first pump assembly;
    b) the sample injector;
    c) the first detector;
    d) the first fluidic routing unit;
    e) the second pump assembly; and
    f) the second detector;
  and
  wherein the chromatography system is configured for first separating the sample in the first separation unit and subsequently introducing at least a portion of the sample eluted from the RPLC column to the second separation unit.

In one variation, the 2D chromatograph system further comprises at least one control device operably connected to one or more of: a) the first pump assembly; b) the sample injector; c) the first detector; d) the first fluidic routing unit; e) the second pump assembly; and f) the second detector.

In some embodiments, provided is a 2D chromatograph system comprising:
  (i) a first separation unit comprising:
    a) a first pump assembly for driving a first mobile phase through the first separation unit,
    b) a sample injector for introducing a sample to the first separation unit;
    c) an RPLC column comprising a C-18 stationary phase (e.g., C-18 silica); and
    d) a first detector;
  (ii) a second separation unit comprising:
    a) a second pump assembly for driving a second mobile phase through the second separation unit,
    b) an SFC column comprising a normal phase stationary phase; and
    c) a second detector;
  (iii) a first fluidic routing unit comprising at least three sample loops, said first fluidic routing unit is connected to the first separation unit and the second separation unit,
    wherein one of the sample loops is in fluidic communication with the first separation unit, another one of the sample loops is in fluidic communication with the second separation unit, and at least one of the sample loops is in fluidic isolation from the first separation unit and the second separation unit;

and wherein at least one of the of sample loops comprises a trapping column, said trapping column comprising a C-18 stationary phase (e.g., C-18 silica);

and, (iv) at least one control device operably connected to one or more of:
   a) the first pump assembly;
   b) the sample injector;
   c) the first detector;
   d) the first fluidic routing unit;
   e) the second pump assembly; and
   f) the second detector;

and wherein the chromatography system is configured for first separating the sample in the first separation unit and subsequently introducing at least a portion of the sample eluted from the RPLC column to the second separation unit.

In one variation, the second separation unit comprises: a) an array of SFC columns, wherein the SFC columns in the array are arranged in a parallel configuration; and b) a second fluidic routing unit for directing flow of the second mobile phase to a desired (or pre-identified) SFC column in the array. In another variation, the second separation unit further comprises a focus column (e.g., a focus column comprising a C-18 stationary phase material (e.g., C-18 silica)) positioned upstream of the SFC column.

In some embodiments, provided is a 2D chromatograph system comprising:

(i) a first separation unit comprising:
   a) a first pump assembly for driving a first mobile phase through the first separation unit,
   b) a sample injector for introducing a sample to the first separation unit;
   c) an RPLC column; and
   d) a first detector;

(ii) a second separation unit comprising:
   a) a second pump assembly for driving a second mobile phase through the second separation unit,
   b) an array of SFC columns, wherein the SFC columns in the array are arranged in a parallel configuration;
   c) a second fluidic routing unit for directing flow of the second mobile phase to a desired (or pre-identified) SFC column in the array; and
   c) a second detector; and, (iii) a first fluidic routing unit comprising at least three sample loops, said first fluidic routing unit is connected to the first separation unit and the second separation unit,
   wherein one of the sample loops is in fluidic communication with the first separation unit, another one of the sample loops is in fluidic communication with the second separation unit, and at least one of the sample loops is in fluidic isolation from the first separation unit and the second separation unit;

and wherein at least one of the of sample loops comprises a trapping column, said trapping column comprising a stationary phase;

and wherein the chromatography system is configured for first separating the sample in the first separation unit and subsequently introducing at least a portion of the sample eluted from the RPLC column to the second separation unit.

In some variations, the RPLC column comprises a C-18 stationary phase (e.g., C-18 silica). In some variations, the SFC column comprises a normal phase silica stationary phase. In some variations, the system further comprises at least one control device operably connected to one or more of:
   a) the first pump assembly;
   b) the sample injector;
   c) the first detector;
   d) the first fluidic routing unit;
   e) the second pump assembly; and
   f) the second detector.

Figure 11:
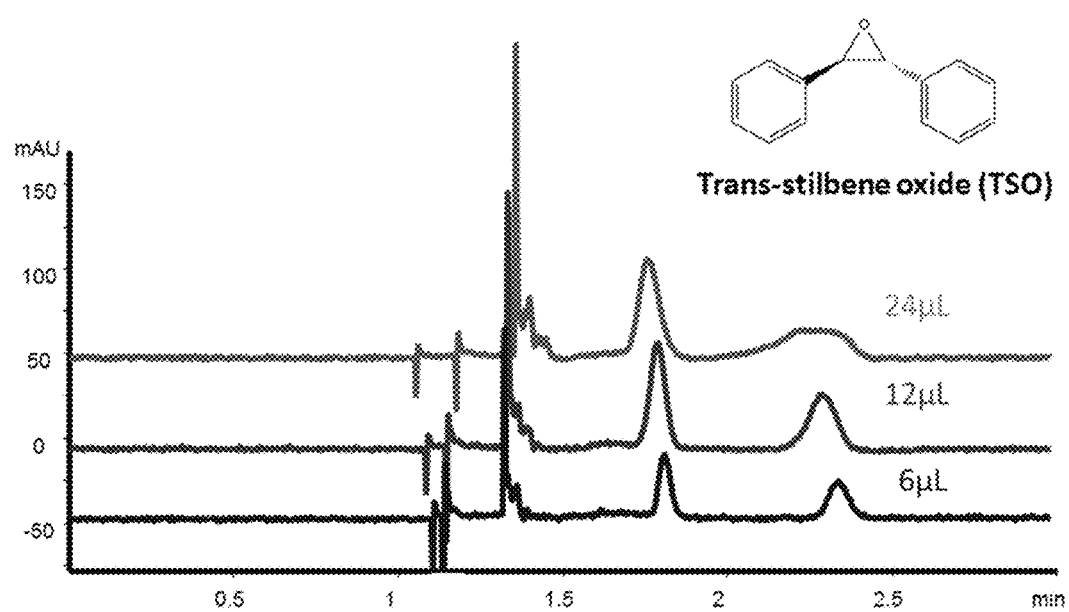
FIG. 11 is an overlay chromatogram of the absorbance measurements (mAU) over time (minutes) for the multidimensional separation of trans-stilbene oxide (TSO) using a system with three sample loop configurations (6 µL, 12 µL, 24 µL).
Figure 12:
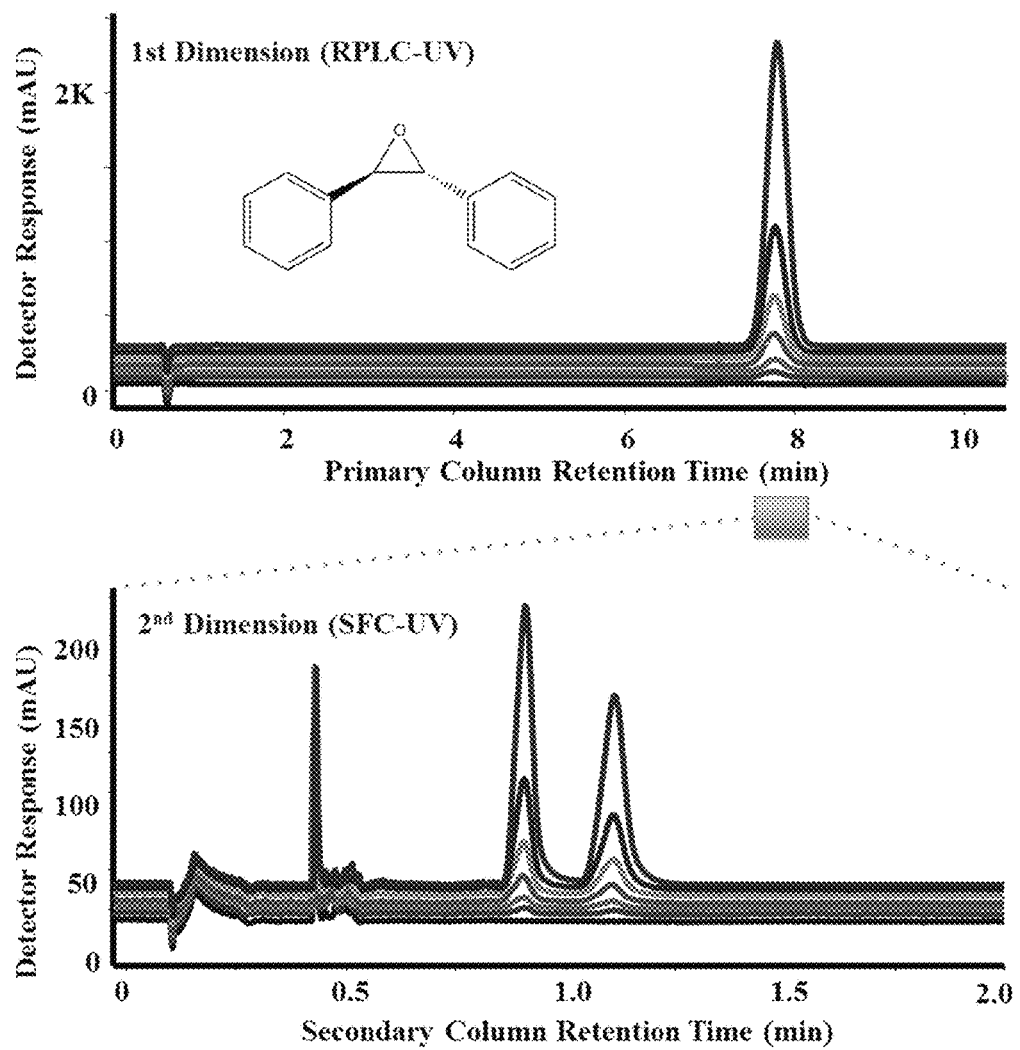
FIG. 12 is an overlay chromatogram of the UV absorbance measurements (mAU) over time (minutes) for the multidimensional separation of an evaluated concentration range (0.005-0.25 mg/ml) of TSO.

The 2D RPLC×SFC system of the present invention address the problem associated with the incompatibility of solvents used in the first dimension RPLC and the second dimension SFC by using a trapping column. The stationary phase in the trapping column retains the analytes while letting the solvents from the RPLC to flow through. This allows the analytes to be concentrated in a small volume for injection into the SFC for further separation. A higher water content in the SFC dimension leads to lower resolution/sensitivity. As demonstrated in Example 2, using a system without a trapping column, only a small fraction can be transferred to the SFC column without adversely affecting the resolution and sensitivity of the SFC analysis (FIG. 11). A transfer volume of 12 µL led to mild broadening of the second peak. When a 24 µL fraction was transferred, a significant broadening of the second peak is observed, which translates to significant loss of sensitivity. In contrast, as shown in Example 3, when a system as depicted in FIGS. 8A and 8B was used, which has a trapping column containing a C-18 stationary phase material (e.g., C-18 silica), a window of 160 µL was transferred, and excellent resolution and sensitivity were obtained (FIG. 12). This system allows for injection of peaks from the first dimension RPLC to the second dimension SFC with minimal impact on the resolution and sensitivity of the SFC analysis. For example, Example 5 compares separation of a chiral drug substance with its enantiomer using a conventional SFC system and a 2D LC-SFC system of the present invention. The results demonstrated that both resolution and sensitivity were preserved in the 2D LC-SFC as compared to conventional SFC. The orthogonal approach, reversed-phase and normal phase conditions in the two dimensions, can be used to increase the confidence level of HPLC peak purity assessment due to the multiplicative peak capacity of the multidimensional system.

Methods of Use

Another factor to consider when developing 2D systems is the ability to operate in an on-line mode. Some advantages of this approach include the ease of automation, reproducibility of the analysis, and the accurate transfer of the fractions from the first to the second dimension without any yield loss or contamination.

An overlooked application of 2D systems is the use in high-throughput analysis. In the pharmaceutical industry for example, Active Pharmaceutical Ingredients (APIs) have to be fully characterized per ICH guidelines. See International Conference on Harmonisation (2006), Q3A(R2): Impurities in New Drug Substances. For purity analysis, two independent analytical methods are developed. A RPLC method usually assesses the achiral purity (impurities and related substances method), and a chiral method that would assess the chiral purity (amount of undesired enantiomer). A 2D system that can generate simultaneous achiral and chiral results would have a huge impact during API process development. Sample preparation, chromatographic analysis times, and data analysis would be reduced to allow higher throughput analysis.

We have previously reported the use of 2D RPLC×RPLC analysis for simultaneous achiral-chiral analysis (*J. Sep. Sci.* 2012, 35:1748). In the API world however, the majority of chiral methods are NPLC methods, and thus a 2D RPLC× NPLC system would have a significant bearing in achieving simultaneous achiral-chiral analysis. As noted above, the incompatibility of the reversed phase and normal phase mobile phases would make this approach very challenging. Supercritical fluid chromatography, a normal phase technique, has also been used for API chiral analysis on analytical as well as preparative scale. In addition to being a "green" technique, SFC is superior to NPLC due to its versatility, higher efficiency, higher throughput, and faster analysis times. Supercritical fluids have low viscosity and high diffusivity (similar to gases) to allow higher flow rates and faster re-equilibration times and have a high density (similar to liquids) to provide a high solvating power. The first on-line 2D LC×SFC was reported by Cortes et al. in 1992 (*J. Microcol. Sep.* 1992, 4:239-244). The interface that Cortes et al. developed is rather complicated and involves multiple stages: elimination of the first dimension solvent by the passage of nitrogen gas, using pressurized $CO_2$ to transfer the analytes onto an impactor interface, and then elution of the analytes from the impactor interface to the SFC capillary column by pressure programming of the $CO_2$ mobile phase. The adoption of this interface for conventional 2D RPLC×SFC separations would be limited due to the solvent elimination step. Cortes et al. used THF (relatively low boiling point, 66° C.) as the LC mobile phase while most conventional RPLC separations are aqueous based.

The present invention demonstrates a new automated interface to couple RPLC and SFC. Thus provided are methods of using the 2D RPLC×SFC chromatography systems described herein for separation and analysis of samples, for example complex sample mixtures which may be difficult to achieve comprehensive analysis by 1D chromatography or other 2D chromatography.

In some embodiments, provided is a method for analyzing a sample (such as a complex sample) using a chromatography system described herein comprising: first separating the complex sample into fractions by reversed-phase liquid chromatography (RPLC); and further separating the fractions from the RPLC dimension by supercritical fluid chromatography (SFC) in the second dimension. Separation in the first dimension (e.g., RPLC on a C-18 stationary phase) relies on differences of certain characters or properties of the components in the complex sample (e.g., hydrophobicity); while separation in the second dimension (e.g., SFC on a normal phase silica gel stationary phase) relies on differences of other characters or properties of the components (e.g., chirality), thus providing better comprehensive analysis than using one-dimensional chromatography.

Developing chiral chromatographic methods for compounds with multiple chiral centers can be challenging as the number of potential stereoisomers increases significantly with the increase in number of the chiral centers (Number of stereoisomers=$2^N$, where N is the number of chiral centers in a compound). Chiral method development is mostly a trial and error process where extensive column and mobile phase screening is done to identify potential hits. However, developing chiral chromatographic methods for compounds with 3 or more chiral centers can be very challenging due to the significant increase in the number of stereoisomers. For pharmaceutical compounds with multiple chiral centers, one common practice is to control the enantiomeric purity of incoming starting materials and demonstrate process control (possibility of epimerization). This would limit the number of potential stereoisomers in the final API. However, this control strategy could be challenged by some regulatory agencies mandating the development of an API chiral method.

The online 2D RPLC×SFC of the present invention allows simultaneous achiral and chiral analysis (analysis by a single sample injection or in the same analytical run) of pharmaceutical samples. The API peak, in a mixture of aqueous and organic content, would be retained on a small volume C-18 trapping column and then back-flushed onto the second dimension SFC column. Thus, in some embodiments, provided is a method for achiral-chiral analysis of a sample comprising a mixture of stereoisomeric components using a chromatography system described herein comprising: resolving diastereomeric components in the sample by RPLC in the first dimension, which provides achiral purity of the sample; and resolving the enantiomeric pairs by SFC in the second dimension in the same analytical run, which further provides chiral purity (% enantiomeric excess) of the components in the sample. The achiral purity of the sample may be determined based on a chromatogram from the RPLC separation, for example, by relative peak area of peaks on a chromatogram obtained on a UV detector of the first separation unit. The chiral purity or enantiomeric excess of each enantiomeric pair may be determined based on a chromatogram from the SFC separation, for example, by relative peak area of peaks on a chromatogram obtained on a UV detector of the second separation unit, or total ion chromatogram obtained on a MS spectrometer attached to the second separation unit.

It is intended and understood that each and every embodiments of the 2D chromatograph system may be used in the methods for analyzing a complex sample or the methods for simultaneous achiral-chiral analysis as if each and every combination is individually described. For example, in some embodiments, provided is a method for simultaneous achiral-chiral analysis of a sample comprising a mixture of stereoisomeric components using a 2D chromatography system, said 2D chromatography system comprising:
 (i) a first separation unit comprising:
  a) a first pump assembly for driving a first mobile phase through the first separation unit,
  b) a sample injector for introducing a sample to the first separation unit;
  c) a reversed-phase liquid chromatography (RPLC) column; and
  d) a first detector;
 (ii) a second separation unit comprising:
  a) a second pump assembly for driving a second mobile phase through the second separation unit,
  b) a supercritical fluid chromatography (SFC) column; and
  c) a second detector;
 and,
 (iii) a first fluidic routing unit comprising a plurality of sample loops, said first fluidic routing unit is connected to the first separation unit and the second separation unit,
  wherein at least one of the plurality of sample loops comprises a trapping column, said trapping column comprising a stationary phase;
said method comprising: first resolving diastereomeric components in the sample by RPLC on the first separation unit, and then resolving the enantiomeric pairs by SFC on the second separation unit in the same analytical run.

In some embodiments, provided is a method for simultaneous achiral-chiral analysis of a sample comprising a mixture of stereoisomeric components using a 2D chromatography system, said 2D chromatography system comprising:
(i) a first separation unit comprising:
  a) a first pump assembly for driving a first mobile phase through the first separation unit,
  b) a sample injector for introducing a sample to the first separation unit;
  c) an RPLC column; and
  d) a first detector;
(ii) a second separation unit comprising:
  a) a second pump assembly for driving a second mobile phase through the second separation unit,
  b) an array of SFC columns, wherein the SFC columns in the array are arranged in a parallel configuration;
  c) a second fluidic routing unit for directing flow of the second mobile phase to a desired (or pre-identified) SFC column in the array; and
  d) a second detector;
and,
(iii) a first fluidic routing unit comprising at least three sample loops, said first fluidic routing unit is connected to the first separation unit and the second separation unit,
  wherein one of the sample loops is in fluidic communication with the first separation unit, another one of the sample loops is in fluidic communication with the second separation unit, and at least one of the sample loops is in fluidic isolation from the first separation unit and the second separation unit;
  and wherein at least one of the of sample loops comprises a trapping column, said trapping column comprising a stationary phase;
said method comprising: first resolving diastereomeric components in the sample by RPLC on the first separation unit, and then resolving the enantiomeric pairs by SFC on the second separation unit in the same analytical run.

In some embodiments, provided is a method for simultaneous achiral-chiral analysis of a sample comprising a mixture of stereoisomeric components using a 2D chromatography system, said 2D chromatography system comprising:
(i) a first separation unit comprising:
  a) a first pump assembly for driving a first mobile phase through the first separation unit,
  b) a sample injector for introducing a sample to the first separation unit;
  c) an RPLC column; and
  d) a first detector;
(ii) a second separation unit comprising:
  a) a second pump assembly for driving a second mobile phase through the second separation unit,
  b) an SFC column; and
  c) a second detector;
(iii) a first fluidic routing unit comprising at least three sample loops, said first fluidic routing unit is connected to the first separation unit and the second separation unit,
  wherein one of the sample loops is in fluidic communication with the first separation unit, another one of the sample loops is in fluidic communication with the second separation unit, and at least one of the sample loops is in fluidic isolation from the first separation unit and the second separation unit;
  and wherein at least one of the of sample loops comprises a trapping column, said trapping column comprising a stationary phase;
and,
(iv) at least one control device operably connected to one or more of:
  a) the first pump assembly;
  b) the sample injector;
  c) the first detector;
  d) the first fluidic routing unit;
  e) the second pump assembly; and
  f) the second detector;
said method comprising: first resolving diastereomeric components in the sample by RPLC on the first separation unit, and then resolving the enantiomeric pairs by SFC on the second separation unit in the same analytical run.

Methods

In another aspect, provided is a method for separating a sample by multi-dimensional chromatography (such as 2D RPLC×SFC) comprising subjecting a portion of a sample captured on a trapping column, said portion is obtained by separating the sample by reversed-phase liquid chromatography (RPLC), said trapping column comprising a stationary phase, to further separation by supercritical fluid chromatography (SFC). In some embodiments, provided is a method for separating a sample comprising the steps of: (i) capturing at least a portion of a sample on a trapping column, said portion is obtained by separating the sample by reversed-phase liquid chromatography (RPLC), said trapping column comprising a stationary phase; and (ii) subjecting the portion of the sample captured on the trapping column to further separation by supercritical fluid chromatography (SFC).

In some embodiments, the method further comprises a step of separating the sample by reversed-phase liquid chromatography (RPLC), comprising: (i) introducing the sample into a first mobile phase; (ii) driving the first mobile phase containing the sample through a RPLC column; and (iii) separating the sample on the RPLC column. In some embodiments, the method further comprises detecting the presence of a component of the sample in the first mobile phase after passing through the RPLC column. In some embodiments, the method further comprises eluting the portion of the sample captured on the trapping column off the trapping column. In some embodiments, the method further comprises detecting a component of the sample after further separation by SFC.

In some embodiments, the method further comprises positioning a trapping column in a flow path of the first mobile phase downstream of the RPLC column for capturing at least a portion of the sample separated by the RPLC column, and/or switching the trapping column carrying the captured portion to a flow path of a second mobile phase for eluting the captured portion off the trapping column. The positioning/switching of the trapping column in/out of the flow path of the mobile phase of the RPLC/SFC unit may be performed in a fluidic routing device interfacing the RPLC unit and the SFC unit in a 2D RPLC×SFC chromatography system.

In some embodiments, the method may be performed on a 2D RPLC×SFC chromatography system configured for countercurrent elution of the analytes captured on the trapping column. In such variation, the first mobile phase flows through the trapping column in a first direction, and the portion of the sample captured on the trapping column is eluted off the trapping column by flowing the second mobile phase through the trapping column in a direction opposite to the first direction. In some embodiments, the method may be performed on a 2D RPLC×SFC chromatography system configured for co-current elution of the analytes captured on the trapping column. In such variation, the first mobile phase flows through the trapping column in a first direction, and the portion of the sample captured on the trapping column is eluted off the trapping column by flowing the second mobile phase through the trapping column in the same direction as the first direction.

In some embodiments, a method for separating a sample with a multi-dimensional chromatography (e.g., a 2D RPLC×SFC chromatography system described herein, or any variations thereof) is provided, comprising the steps of:
(i) introducing a sample into a first mobile phase;
(ii) driving the first mobile phase containing the sample through a RPLC column;
(iii) separating the sample on the RPLC column;
(iv) detecting the presence of a component of the sample in the first mobile phase after passing through the RPLC column;
(v) capturing on a first trapping column at least a first portion of the sample separated on the RPLC column, said first trapping column comprising a stationary phase;
(vi) eluting the first portion of the sample captured on the first trapping column off the first trapping column;
(vii) subjecting the first portion of the sample captured on the first trapping column to further separation by SFC; and
(viii) detecting a component of the sample after further separation by SFC.

In some instances of 2D chromatography, such as in the comprehensive or pseudo-comprehensive mode, more than one fractions from the first dimension RPLC may be captured one or more trapping columns and released for analysis in the second dimension SFC. Thus in some embodiments, the method further comprises the steps of:
(ix) capturing on a second trapping column at least a second portion of the sample separated on the RPLC column, said second trapping column comprising a stationary phase;
(x) eluting the second portion of the sample captured on the second trapping column off the second trapping column;
(xi) subjecting the second portion of the sample captured on the second trapping column to further separation by SFC.
These steps may be repeated multiple times for capturing/releasing multiple fractions.

In some embodiments, provided is a method for separating a sample using a multi-dimensional chromatography (e.g., a 2D RPLC×SFC chromatography system described herein, or any variations thereof), comprising the steps of:
(i) introducing a sample into a first mobile phase;
(ii) driving the first mobile phase containing the sample through a RPLC column;
(iii) separating the sample on the RPLC column;
(iv) detecting the presence of a component of the sample in the first mobile phase after passing through the RPLC column;
(v) positioning a trapping column in a flow path of the first mobile phase downstream of the RPLC column;
(vi) capturing on the trapping column at least a portion of the sample separated on the RPLC column, said trapping column comprising a stationary phase;
(vii) switching the trapping column carrying the captured portion into a flow path of a second mobile phase;
(viii) eluting the portion of the sample captured on the trapping column off the trapping column;
(ix) subjecting the portion of the sample captured on the trapping column to further separation by SFC; and
(x) detecting a component of the sample after further separation by SFC.

In some embodiments, steps (i) through (x) are performed in the order as listed. In some embodiments, the steps (iv) through (x) are repeated for one or more times until all fractions of interests are analyzed.

In some of these embodiments, the RPLC column comprises a reversed-phase stationary phase, for example, a stationary phase comprising a reversed-phase material such as a C-18 phase (e.g., a C-18 silica), a C-8 phase (e.g., a C-8 silica), a C-4 phase (e.g., a C-4 silica), or other reversed-phase materials described herein. In some of these embodiments, the stationary phase in the trapping column comprises a reversed-phase material such as a C-18 phase (e.g., a C-18 silica), a C-8 phase (e.g., a C-8 silica), a C-4 phase (e.g., a C-4 silica), or other reversed-phase materials described herein.

In some of these embodiments, the SFC separation is performed on a SFC column comprising a normal phase stationary phase, for example, a stationary phase comprising a normal phase silica gel or other normal phase materials described herein. In some of these embodiments, the SFC separation is performed on a SFC column selected from an array of SFC columns arranged in parallel, each SFC column in the array may comprise a stationary phase that may be the same or different. The stationary phase material in the SFC column may be adapted for separating the specific components in the sample.

In some of these embodiments, the method may further comprise focusing the analytes eluted from the fraction captured on the trapping column on a focus column prior to further separation on the SFC column. The focus column comprises a stationary phase that may or may not be the same as the stationary phase used in the trapping column. In some embodiments, the focus column is loaded with a stationary phase comprising a reversed-phase material such as a C-18 phase, a C-8 phase, a C-4 phase or other reversed-phase materials described herein.

The methods for separating a sample described herein may be adapted for performance on a 2D RPLC×SFC chromatography system described herein or any embodiments or variations thereof described.

EXAMPLES

The following Examples are provided to illustrate but not to limit the invention.

Chemicals and Regents

Carbon dioxide ($CO_2$) was obtained from Praxair (Danbury, Conn., USA). Acetonitrile (ACN) was purchased from Avantor's J.T. Baker (Center Valley, Pa., USA). Methanol (MeOH), isopropyl alcohol (IPA), ethyl alcohol (EtOH), 98.0%—100.0% formic acid, and 28.0%—30.0% ammonium hydroxide ($NH_4OH$) were purchased from EMD chemicals (Gibbstown, N.J., USA). Ammonium formate was purchased from Sigma Aldrich (St. Louis, Mo., USA). HPLC grade Millipore water was obtained from Purelab ultra Millipore water dispenser. Trans-stilbene oxide (TSO) was purchased from TCI (Tokyo, Japan). Drug substance A used in this study was synthesized by the process chemistry department at Genentech, CA, USA.

Example 1—Instrumentation

The analytical instrument is a customized two-dimensional 1260 2D-LC-SFC system with mass spectrometer from Agilent Technologies (Santa Clara, Calif., USA). The RPLC unit consists of an Agilent 1260 quaternary pump (G1311B), a 1260 HiP ALS auto-sampler (G1367E), and an Agilent 1260 multi-wavelength UV detector (G1365C). Stainless steel fittings and tubing are used throughout the system due to high pressure considerations. The SFC unit consists of a 1260 SFC binary pump (G4302A) with a three position solvent control valve, a 1260 HiP degasser (G4225A), a 1290 thermostated column compartment (G1316C), an eight-position Agilent 1290 infinity valve drive (G1170A), an Agilent 1260 DAD (G1315C) equipped with a high-pressure flow cell, and an Agilent 1260 infinity SFC control module (G4301A). Part of the SFC flow was directed towards an Agilent 6120 quadrupole MS. An Agilent 1260 iso pump (G1310B) was used to generate a make-up flow of 0.15 mL/min in order to compensate for the loss of $scCO_2$. An Agilent 1290 Flexcube (G4227A) was installed to enable multiple peak parking on different trapping columns using a custom built 12-port switching valve. Instrument control and data collection was done with Agilent Chemstation software (Santa Clara, Calif., USA).

Figure 10:
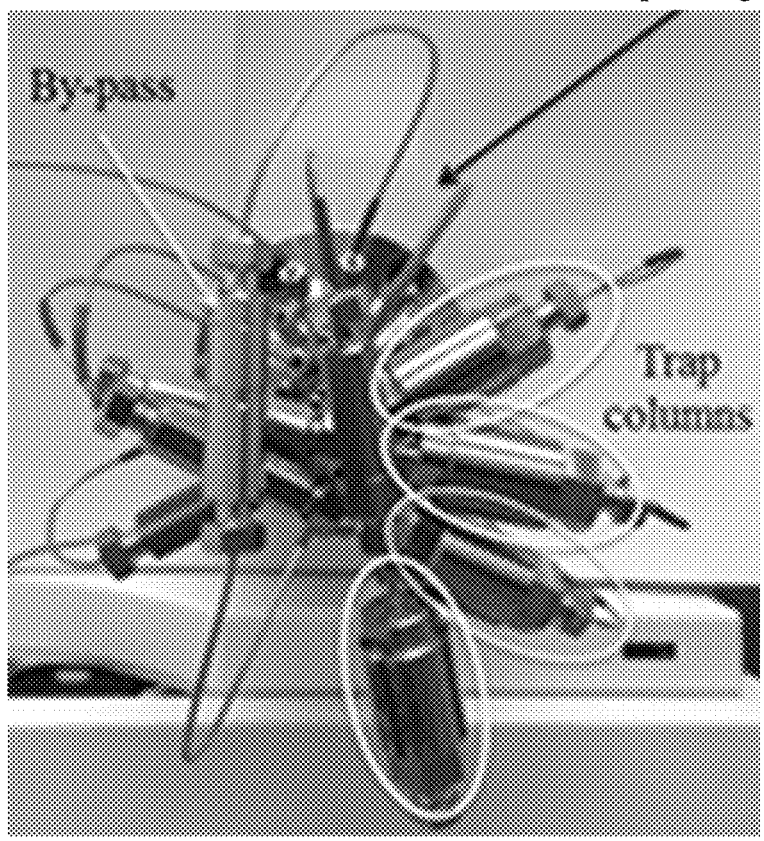
FIG. 10 is a photographic image of an exemplary parking deck valve.

FIG. 10 is a photographic image of an exemplary parking deck valve (e.g., valve V2 featured in FIG. 9). As shown in FIG. 10, there are four trapping columns that may be used for peak parking. Additionally, as depicted, there is a by-pass loop that allows for either the mobile phase originating from the first separation unit or the mobile phase originating from the second separation unit to be directed downstream without passing through a trapping column.

Example 2

The primary objective of this study was to evaluate the effect of the volume of the mobile phase transferred from the first dimension to the second dimension on the resolution of the separation in the second dimension (SFC). Here, a multidimensional chromatography system was used to separate the enantiomers of trans-stilbene oxide (TSO). The first dimension (RPLC) was interfaced with the second dimension (SFC) using a valve with a sample loop lacking a trapping column. The sample loop was used to store a selected volume of the first mobile phase containing a portion of the sample eluted from the first dimension. Subsequently, the volume of the first mobile phase stored in the sample loop was transferred to the second dimension for further separation. Sample loops allowing for the storage, and subsequent transfer, of 6 µL, 12 µL, and 24 µL of mobile phase were used.

For the first RPLC dimension, an ACQUITY UPLC HSS T3 1.8 µm 2.1×50 mm column was utilized under an isocratic condition with 90/10 ACN/water at a flow rate of 0.2 mL/min. UV detection was done at 225 nm.

For the second SFC dimension, a Chiralcel OD3 3.0 µm 4.6 mm×50 mm column was utilized at 40° C. with an isocratic flow of 95:5 $scCO_2$ (MPA)/IPA with 0.1% NH4OH (MPB). The flow rate was 4.0 mL/min with an outlet pressure of 130 bar and nozzle temperature of 60° C.

The trapping loop for this experiment was a flex capillary (0.5 mm×150 mm with an internal volume of approximately 29 µL). The three switching times were 0.03 min, 0.06 min, and 0.12 min corresponding to 6 µL, 12 µL, and 24 µL transfer volumes, respectively (based on a flow rate of 0.2 mL/min).

FIG. 11 is a compilation chromatograph of the UV absorbance measurements (mAU) over time (minutes) for the multidimensional separation of TSO using a system with three sample loop configurations (6 µL, 12 µL, 24 µL). As illustrated in FIG. 11, increasing the transfer volume of the first mobile phase to the second dimension reduces the resolution and sensitivity in the second dimension.

Example 3

In this example, the efficiency of transferring a sample from a first dimension (RPLC) to a second dimension (SFC) using an interface containing a trapping column was evaluated.

Solutions of TSO standard ranging from 0.005 mg/mL to 0.25 mg/ml were analyzed using the 2D LC-SFC system illustrated in FIG. 8A and FIG. 8B. The second detector was a UV detector. Based on the results from Example 2, a C18-reversed-phase trapping column of low internal volume was evaluated.

The reversed-phase chromatograph utilized in the first dimension was an Acquity UPLC HSS T3 column (50×2.1 mm, 1.8 µm) from Waters Corporation (Milford, Mass., USA). The separation in the first dimension was run under isocratic conditions with 50:50 (0.05% formic acid in water):(0.05% formic acid in ACN) at a flow rate of 0.2 mL/min. The RPLC column was placed in the SFC thermal column compartment at 40° C. UV detection was done at 225 nm. The first dimension injection volume was 5 µL.

The supercritical fluid chromatograph used in the second dimension was a Chiralcel OD3 column (50×4.6 mm, 3.0 µm) from Chiral Technologies (West Chester, Pa., USA). The separation in the second dimension was run under an isocratic flow of 95:5 ($scCO2$):(isopropyl alcohol with 0.1% ammonium hydroxide). The column temperature used was 40° C. and the flow rate was set at 4.0 mL/min with an outlet pressure of 130 bar and nozzle temperature of 60° C. Using the focusing column at the head of SFC column is optional.

As discussed above, a low volume trapping column was used in the interface of the two dimensions. Specifically, the trapping column used was a SunShell C18 column (5.0×1.0 mm, 5 µm) from ChromaNik Technologies (Osaka, Japan).

TSO standard solutions (0.25, 0.1, 0.05, 0.025, 0.01, 0.005 mg/mL) were prepared in 50:50 ACN/water. A window of 0.8 min (~160 µL) across the apex of the TSO peak was transferred to the trapping column that was conditioned with initial SFC conditions (100% $scCO_2$). An initial hold at 0% (IPA with 0.1% NH4OH) was maintained for first 0.2 min after the switch and then increased to 5% (IPA with 0.1% NH4OH) in 0.1 min with a 2.35 min hold. The column was re-equilibrated with 0% (IPA with 0.1% NH4OH) for 0.2 min. Samples were run in triplicates. Detection in the second dimension was done by UV detection at 225 nm.

FIG. 12 is a compilation chromatograph of the UV absorbance measurements (mAU) over time (minutes) for the multidimensional separation of varying concentrations of TSO. The top chromatogram was measured following separation in the first dimension. Enantiomers of TSO standard are observed to co-elute in the reverse phase primary column. The peak eluting from the primary column post detection was diverted to the trapping column and back-flushed into the secondary column for further separation. As shown in FIG. 12, the bottom chromatograph was measured following separation in the second dimension.

Here, enantiomers of TSO standard are observed to be baseline resolved in the secondary chiral column.

Furthermore, as illustrated in FIG. 12, overlay plots demonstrated the linearity of detector response over the evaluated concentration range with a correlation coefficient greater than 0.99 (data not shown). In a different study, volumes ranging from 10 to 100 μL (by timing valve V1) were transferred to the secondary SFC column. The results of this study showed linear response over the evaluated range (results not shown).

Example 4

In this example, the 2D LC-SFC system described in Example 3 was further tested to demonstrate the ability of simultaneous achiral-chiral analysis of a sample of Drug Substance A.

The reversed-phase chromatogram utilized in the first dimension was a SunFire C18 column (150×3.0 mm, 3.5 μm) from Waters Corporation (Milford, Mass., USA) at a temperature of 40° C. MPA was 5 mM ammonium formate, pH 3.3 and MPB was 0.05% formic acid in ACN. MP program for the RPLC column was 5% B to 25% B in 5 min, to 29% B in 25 min, to 90% B in 30 min, and then re-equilibration at 5% B for 5 min. The flow rate was set to 1.0 mL/min. The first dimension UV detection was done at 340 nm. The first dimension injection volume was 5 μL.

The supercritical fluid chromatogram used in the second dimension was a Chiralpak IC3 column (50×4.6 mm, 3 μm) from Chiral Technologies (West Chester, Pa., USA) at 40° C. with an initial MP flow of 65:35 scCO$_2$ (MPA)/methanol with 0.1% ammonium hydroxide (MPB). The flow rate was 4.0 mL/min with an outlet pressure of 130 bar and nozzle temperature of 60° C. Four Zorbax Eclipse XDB-C18 columns (5.0×2.1 mm, 1.8 μm) from Agilent Technologies (Santa Clara, Calif., USA) were used as the trapping column.

A sample of Drug Substance A was prepared at 0.5 mg/mL in 25:75 ACN/water with 0.05% FA. A window of 0.1 min (100 μL) across the apex was transferred to the pre-conditioned trapping column. The SFC column was maintained at an isocratic hold (35% MPB) for 0.5 min, then to 55% B in 2 min with a 3 min hold. The column was re-equilibrated at 35% B for 0.2 min. Detection in the second dimension was done by SIM-MS detection at 565 m/z.

Figure 13:
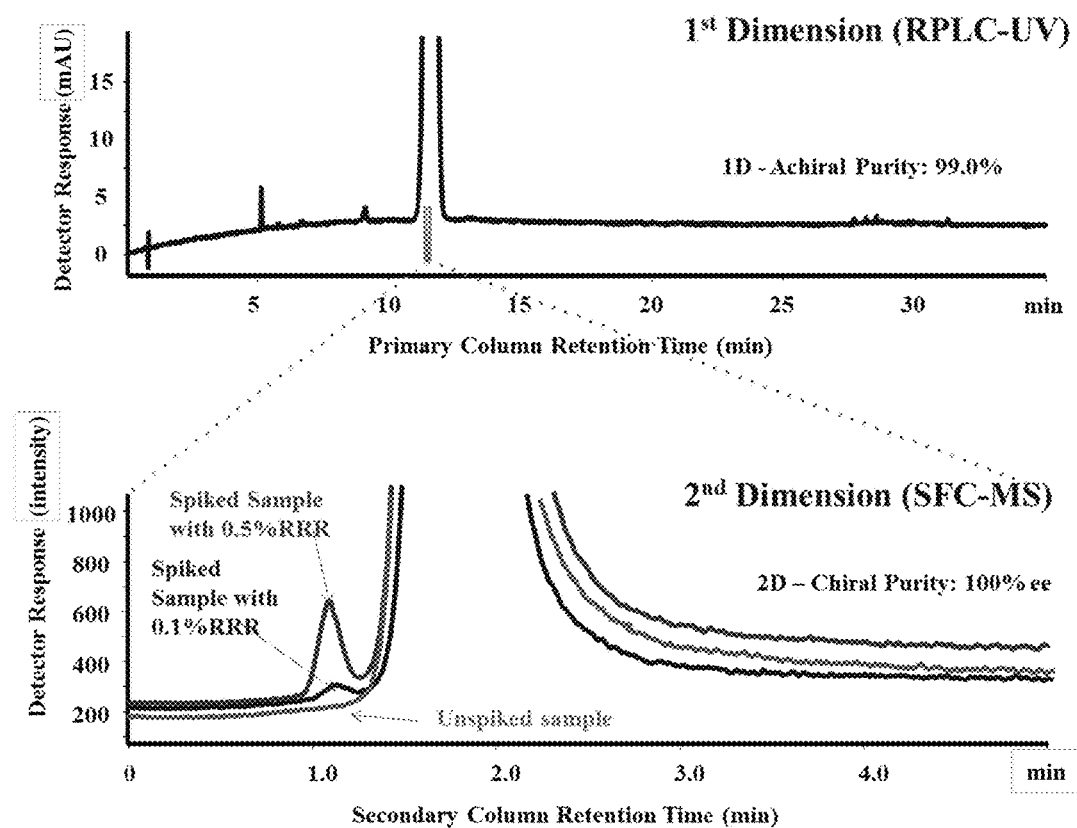
FIG. 13 is an overlay chromatogram of unspiked and spiked analyses of a sample of Drug Substance A obtained from a 2D RPLC-SFC system.

As depicted in FIG. 13, the achiral and chiral purity results were 99.0% and 100% enantiomeric excess (% ee), respectively. An overlay plot of unspiked sample with no enantiomer detected (bottom), sample spiked with 0.1% of the undesired enantiomer (middle), and a sample spiked with 0.5% undesired enantiomer (top) demonstrated the capability of this system to detect the undesired enantiomer at 0.1% levels.

Example 5

The present study was performed to demonstrate the comparability of both sensitivity and resolution between the second dimension SFC in a 2D LC-SFC system and conventional (1D) SFC.

The 2D LC-SFC system was the same as the system used in Example 4. The mobile phase program and switching time were modified. In the first dimension, the mobile phase program was 25% B for 5 min, 25% to 90% B by 15 min, and then re-equilibrated at 25% B for 5 min. A window of 0.1 min (100 μL) at the apex of the peak was transferred to the trapping column. The conditions for conventional SFC were the same as those used in the second dimension of 2D LC-SFC (described in Example 4).

Figure 14A:
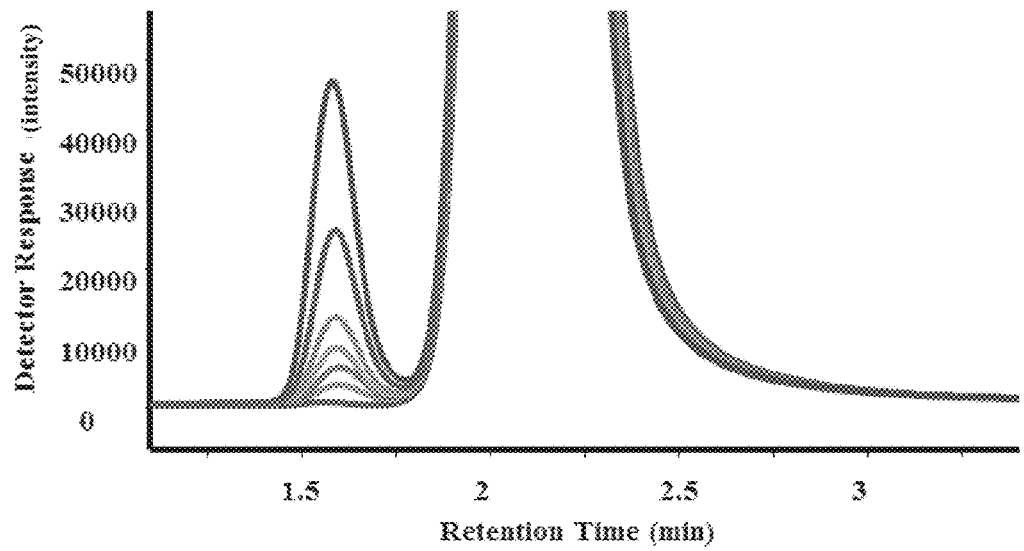
FIG. 14A and FIG. 14B are conventional SFC and 2D RPLC-SFC chromatograms, respectively, of a sample of Drug Substance A containing varying levels of an undesired enantiomer (0.1 to 2.0% range).
Figure 14B:
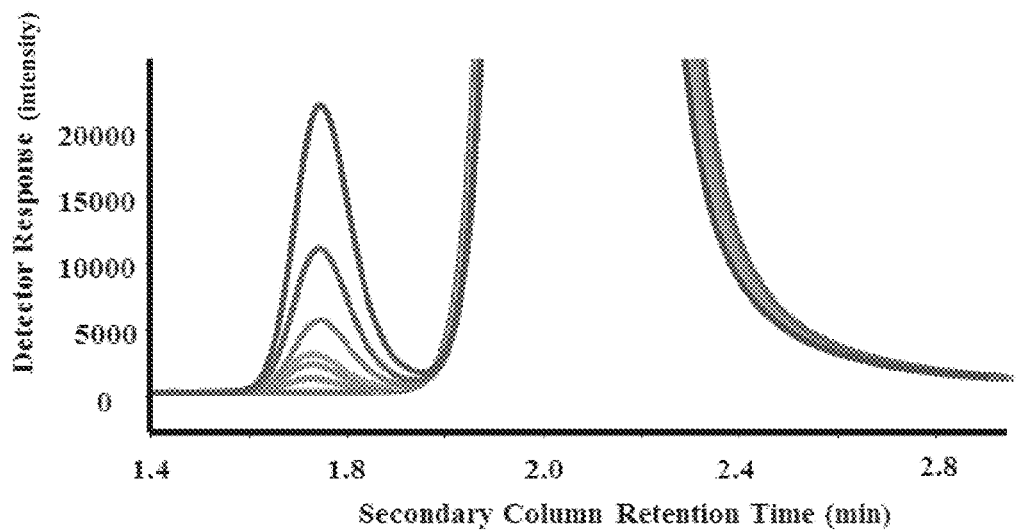

Standard solutions of a sample of Drug Substance A containing varying levels of the undesired enantiomer (0.1 to 2.0% range) were analysed using both techniques (2D LC-SFC and SFC). An overlay of the standard chromatograms from SFC and 2D LC-SFC techniques are shown in FIG. 14A and FIG. 14B, respectively. The results illustrated comparable separations obtained with both techniques. Both resolution and sensitivity were preserved in the 2D LC-SFC as compared to conventional SFC.

As demonstrated in Example 2, introduction of reversed-phase mobile phase into the SFC dimension deleteriously affects resolution and sensitivity of SFC separation. Although reversed-phase mobile phase is still introduced into the SFC dimension with the 2D LC-SFC system described here, use of a trapping column allows for an LC-SFC interface that does not compromise downstream SFC separation.

Example 6

In this example, a complex chiral chromatographic separation of desired sensitivity and selectivity in a single analysis is demonstrated.

Drug Substance A has three chiral centers and hence has four pairs of diastereomers (eight potential stereoisomers). A mixture of the 4 diastereomeric pairs was prepared in 30/70 ACN/water at 0.05 mg/mL. Ratio of the two enantiomers in each pair (RRS/SRR, SRS/RSR, SSS/RRR; RRS/SSR) was approximately 2:1.

Separation of each stereoisomer was achieved using the 2D LC-SFC system shown in FIG. 9. The experimental conditions in the primary column were same as one described in section Example 4. Four trapping columns were used with the Flexcube (Agilent) in the secondary dimension to trap the 4 diastereomeric pairs. Following sample injection, trapping columns were conditioned with 60:40 scCO$_2$ (MPA)/methanol with 0.1% ammonium hydroxide (MPB) for one min with the exception of trapping column 2 which was conditioned with 65:35 scCO$_2$ (MPA)/methanol with 0.1% ammonium hydroxide (MPB). Primary column eluent corresponding to 0.1 min (100 μL) window at the apex of the diastereomeric peaks at 10.55 min, 10.95 min, 11.80 min and 13.30 min were sequentially transferred into four trapping columns. Trapped components were sequentially chromatographed starting at 14.0 min, 18.0 min, 23.5 min and 27.5 min respectively in the secondary dimension. An initial hold at 60:40 scCO$_2$ (MPA)/methanol with 0.1% ammonium hydroxide (MPB) was maintained for first 0.5 min after the switch and then increased to 40:60 scCO$_2$ (MPA)/methanol with 0.1% ammonium hydroxide (MPB) in 2.5 min with a 0.3 min hold with the exception of trapped component 2. For component 2, the initial hold at 65:35 scCO$_2$ (MPA)/methanol with 0.1% ammonium hydroxide (MPB) was maintained for first 1 min after the switch and then increased to 55:45 scCO$_2$ (MPA)/methanol with 0.1% ammonium hydroxide (MPB) in 3.0 min with a 0.3 min hold. Detection in the second dimension was done by SIM-MS detection at 565 m/z.

Figure 15:
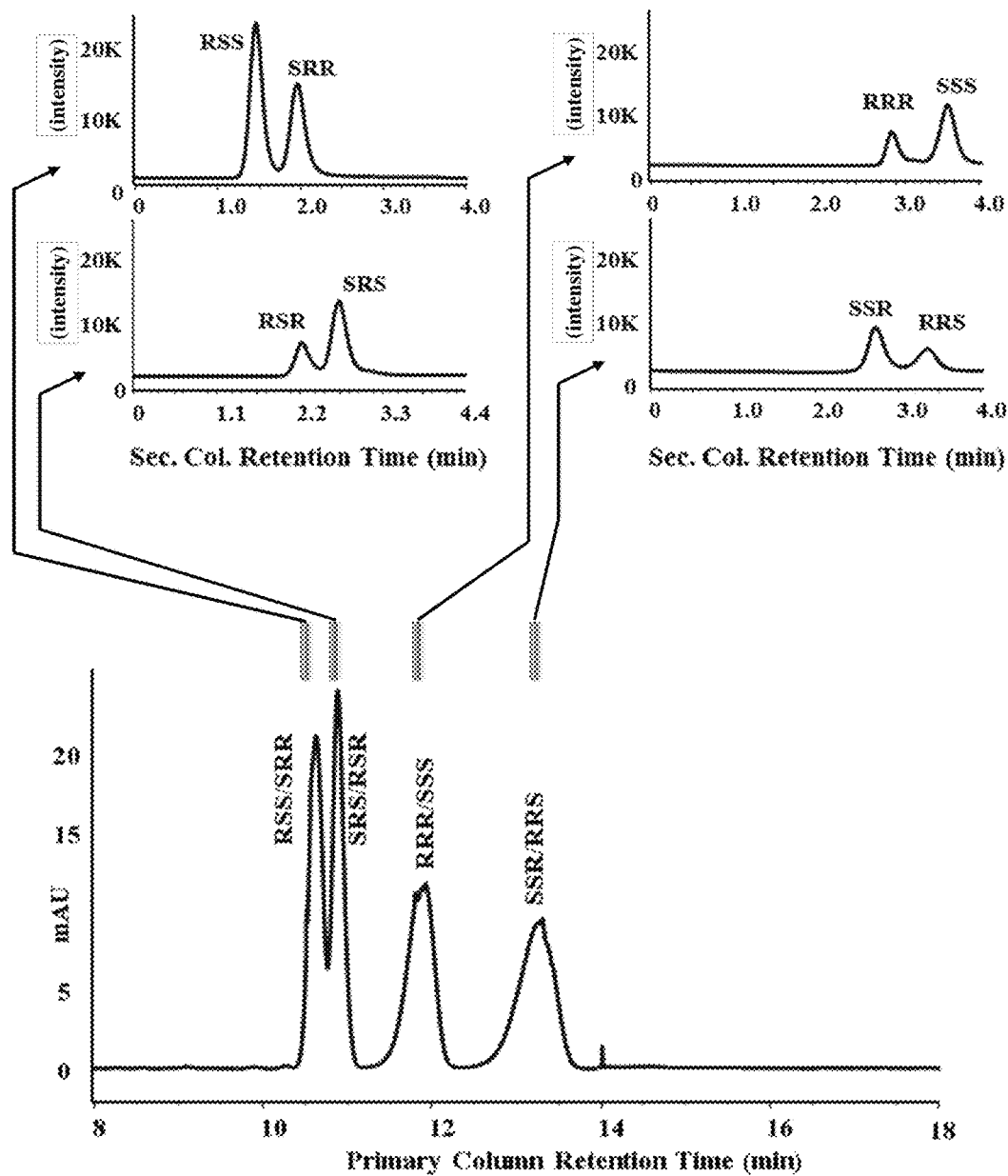
FIG. 15 is a series of chromatograms illustrating the separation of 8 stereoisomers of a sample of Drug Substance A using a 2D RPLC-SFC system. The lower chromatogram shows the separation of 4 diastereomeric pairs of a sample of Drug Substance A in the first RPLC dimension. The four upper chromatograms demonstrate that each diastereomeric pair was further separated in the second SFC dimension.

As illustrated in FIG. 15, the primary achiral RPLC column resolves the four diastereomeric pairs (RSS/SRR, SRS/RSR, RRR/SSS, SSR/RRS) and other process related impurities from the API providing achiral purity. Each of these diastereomeric pair is then sequentially transferred from the primary RPLC column (post detection) to four different trapping columns in Valve 2 (V2; FIG. 9). The trapped diastereomeric fractions are then sequentially back-flushed and analysed on the secondary SFC chiral column providing chiral purity. By presenting a simpler sample mixture to the secondary chiral column, potential stereoisomers are more efficiently resolved. As shown in FIG. 15, eight stereoisomers, corresponding to the four-diastereomeric pairs, were successfully resolved on the secondary SFC dimension using MS detection. Using the parking deck valve, the application of the 2D LC-SFC is extended to the analysis of compounds with multiple chiral centers that are difficult to resolve by conventional chiral chromatography.

Example 7

The present study was performed to test a 2D LC-SFC system wherein a focus column is placed at the head of the SFC column.

The 2D LC-SFC conditions were the same as those described in Example 3. Furthermore, the TSO samples were prepared in the same manner as described in Example 3. In short, TSO standard solutions (0.25, 0.1, 0.05, 0.025, 0.01, 0.005 mg/mL) were prepared in 50:50 ACN/water. The first dimension injection volume was 5 µL. In addition, for those analyses complete with a focusing column, a focusing column was placed at the head of the SFC column. The focusing column used was Pursuit XRs C18 (20×2.0 mm, 5 um) from Agilent Technologies (Santa Clara, Calif., USA).

Figure 16:
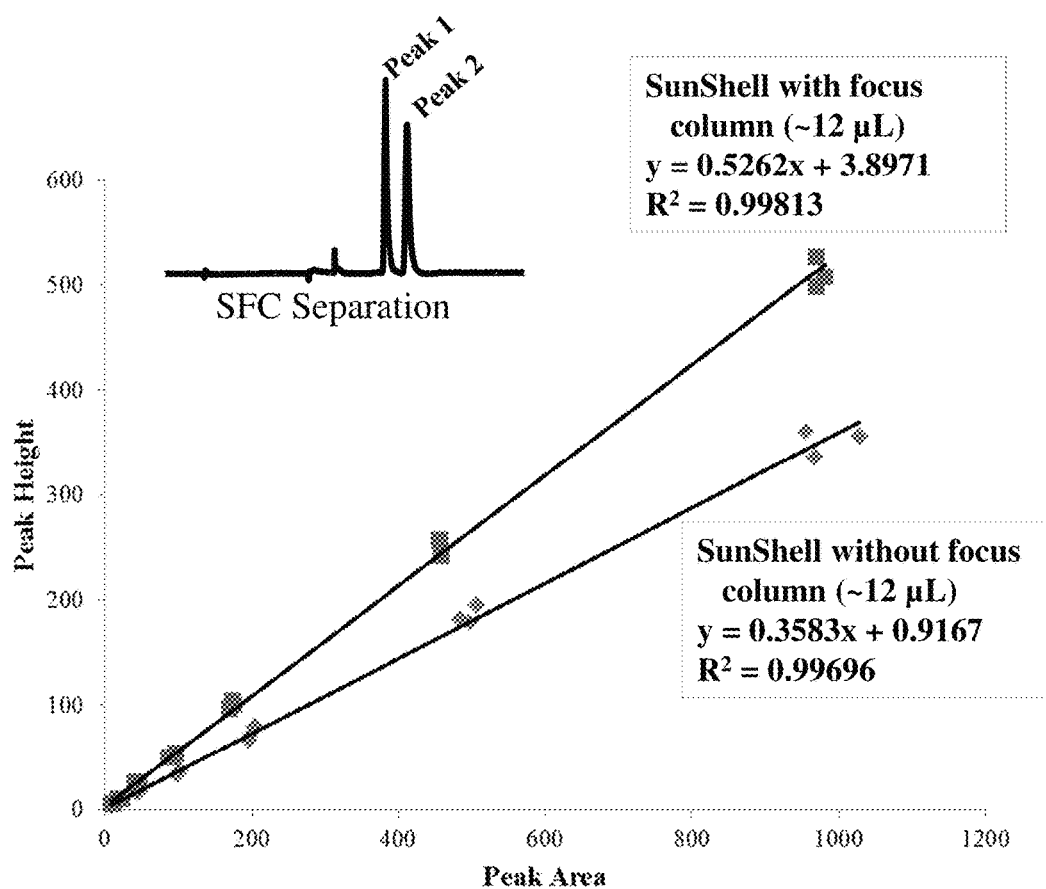
FIG. 16 is a plot of peak height versus peak area from analyses of TSO over a concentration range using a 2D RPLC-SFC system with and without a focus column located at the upstream head of the SFC column.

The 2D LC-SFC separation of a series of concentrations of a TSO standard with and without a focusing column is shown in FIG. 16. The TSO enantiomers are baseline resolved in both conditions. Using a focusing column however, resulted in increasing the slope of peak height v/s peak area plot improving the signal to noise (S/N) ratio in the second dimension (peak 1). Similar results were observed for peak 2 (data not shown).

EXEMPLARY EMBODIMENTS

The invention is further described by the following embodiments. The features of each of the embodiments are combinable with any of the other embodiments where appropriate and practical.

Embodiment 1

In one embodiment, the invention provides a chromatography system for separating a sample comprising:
a first separation unit comprising:
  a) a first pump assembly for driving a first mobile phase through the first separation unit,
  b) a sample injector for introducing a sample to the first separation unit; and
  c) a reversed-phase liquid chromatography (RPLC) column;
a second separation unit comprising:
  a) a second pump assembly for driving a second mobile phase through the second separation unit, and
  b) a supercritical fluid chromatography (SFC) column; and,
a first fluidic routing unit comprising a plurality of sample loops, said first fluidic routing unit is connected to the first separation unit and the second separation unit, wherein at least one of the plurality of sample loops comprises a trapping column, said trapping column comprising a stationary phase;
and
wherein the chromatography system is configured for first separating the sample in the first separation unit and subsequently introducing at least a portion of the sample eluted from the RPLC column to the second separation unit.

Embodiment 2

In a further embodiment of embodiment 1, the first fluidic routing unit comprises two sample loops; wherein one of the two sample loops is in fluidic communication with the first separation unit and the other one of the two sample loops is in fluidic communication with the second separation unit.

Embodiment 3

In a further embodiment of embodiment 1, wherein the first fluidic routing unit comprises at least three sample loops, and wherein at least one of the sample loops is in fluidic isolation from the first separation unit and the second separation unit.

Embodiment 4

In a further embodiment of embodiment 3, at least one sample loop comprising a stationary phase material is in fluidic isolation from the first separation unit and the second separation unit.

Embodiment 5

In a further embodiment of embodiment 1, the first fluidic routing unit comprises a plurality of trapping columns each positioned in a sample loop.

Embodiment 6

In a further embodiment of any one of embodiments 1 to 5, the first fluidic routing unit is configured to allow fluid flow through a sample loop in a first direction when said sample loop is positioned in fluidic communication with the first separation unit and to allow fluid flow through said sample loop in a direction opposite to the first direction when said sample loop is positioned in fluidic communication with the second separation unit.

Embodiment 7

In a further embodiment of any one of embodiments 1 to 5, the first fluidic routing unit is configured to allow fluid flow through a sample loop in a first direction when said sample loop is positioned in fluidic communication with the first separation unit and to allow fluid flow through said sample loop in a direction same as the first direction when said sample loop is positioned in fluidic communication with the second separation unit.

Embodiment 8

In a further embodiment of any one of embodiments 1 to 7, the RPLC column comprises a reversed-phase stationary phase.

Embodiment 9

In a further embodiment of embodiment 8, the reversed-phase stationary phase comprises a C-18 phase (e.g., C-18 silica).

Embodiment 10

In a further embodiment of embodiment 8 or 9, the stationary phase in the trapping column comprises a reversed-phase material.

Embodiment 11

In a further embodiment of embodiment 9, the reversed-phase material comprises a C-18 phase (e.g., C-18 silica).

Embodiment 12

In a further embodiment of any one of embodiments 1 to 11, the second separation unit comprises one SFC column.

Embodiment 13

In a further embodiment of embodiment 12, the SFC column comprises a normal phase stationary phase.

Embodiment 14

In a further embodiment of embodiment 13, the normal phase stationary phase comprises a silica gel.

Embodiment 15

In a further embodiment of any one of embodiments 1 to 14, the second separation unit further comprises a focus column located upstream of the SFC column.

Embodiment 16

In a further embodiment of embodiment 15, the focus column comprises a reversed-phase material.

Embodiment 17

In a further embodiment of any one of embodiments 1 to 11, the second separation unit comprises: a) an array of SFC columns, wherein the SFC columns in the array are arranged in a parallel configuration; and b) a second fluidic routing unit for directing flow of the second mobile phase to a desired (or pre-identified) SFC column in the array.

Embodiment 18

In a further embodiment of embodiment 17, the second separation unit further comprises a focus column located upstream of each SFC column in the array of SFC columns.

Embodiment 19

In a further embodiment of any one of embodiments 1 to 18, further comprising a first detector positioned downstream of the RPLC column.

Embodiment 20

In a further embodiment of any one of embodiments 1 to 19, further comprising a second detector positioned downstream of the SFC column.

Embodiment 21

In a further embodiment of any one of embodiments 1 to 20, further comprising at least one control device operably connected to one or more of: a) the first pump assembly; b) the sample injector; c) the first detector; d) the first fluidic routing unit; e) the second pump assembly; and f) the second detector.

Embodiment 22

In one embodiment, the invention provides a method for separating a sample comprising the steps of:
(i) capturing at least a portion of a sample on a trapping column, said portion is obtained by separating the sample by reversed-phase liquid chromatography (RPLC), said trapping column comprising a stationary phase; and
(ii) subjecting the portion of the sample captured on the trapping column to further separation by supercritical fluid chromatography (SFC).

Embodiment 23

In a further embodiment of embodiment 22, further comprising separating the sample with a reversed-phase liquid chromatography comprising:
(i) introducing the sample into a first mobile phase;
(ii) driving the first mobile phase containing the sample through a RPLC column; and
(iii) separating the sample on the RPLC column.

Embodiment 24

In a further embodiment of embodiment 23, further comprising detecting the presence of a component of the sample in the first mobile phase after passing through the RPLC column.

Embodiment 25

In a further embodiment of any one of embodiments 22 to 24, further comprising eluting the portion of the sample captured on the trapping column off the trapping column.

Embodiment 26

In a further embodiment of any one of embodiments 22 to 25, further comprising detecting a component of the sample after further separation by SFC.

Embodiment 27

In a further embodiment of any one of embodiments 22 to 26, further comprising positioning a trapping column in a flow path of the first mobile phase downstream of the RPLC column for capturing at least a portion of the sample separated by the RPLC column.

Embodiment 28

In a further embodiment of embodiment 27, further comprising switching the trapping column carrying the captured portion to a flow path of a second mobile phase for eluting the captured portion off the trapping column.

Embodiment 29

In a further embodiment of embodiment 28, the step of positioning the trapping column in the flow path of the first mobile phase or the step of switching the trapping column to the flow path of the second mobile phase is performed in a fluidic routing unit interfacing a fluidic path of the PRLC and a fluidic path of the SFC.

Embodiment 30

In a further embodiment of any one of embodiments 22 to 29, further comprising re-capturing at least a portion of the sample eluted off the trapping column on a focus column prior to further separation by SFC.

Embodiment 31

In a further embodiment of any one of embodiments 22 to 30, the first mobile phase flows through the trapping column in a first direction, and the portion of the sample captured on the trapping column is eluted off the trapping column by flowing the second mobile phase through the trapping column in a direction opposite to the first direction.

Embodiment 32

In a further embodiment of any one of embodiments 22 to 30, the first mobile phase flows through the trapping column in a first direction, and the portion of the sample captured on the trapping column is eluted off the trapping column by flowing the second mobile phase through the trapping column in a direction same as the first direction.

Embodiment 33

In a further embodiment of embodiment 22, comprising the steps of:
(i) introducing a sample into a first mobile phase;
(ii) driving the first mobile phase containing the sample through a RPLC column;
(iii) separating the sample on the RPLC column;
(iv) detecting the presence of a component of the sample in the first mobile phase after passing through the RPLC column;
(v) capturing on a first trapping column at least a first portion of the sample separated on the RPLC column, said first trapping column comprising a stationary phase;
(vi) eluting the first portion of the sample captured on the first trapping column off the first trapping column;
(vii) subjecting the first portion of the sample captured on the first trapping column to further separation by SFC; and
(viii) detecting a component of the sample after further separation by SFC.

Embodiment 34

In a further embodiment of embodiment 33, further comprising the steps of:
(ix) capturing on a second trapping column at least a second portion of the sample separated on the RPLC column, said second trapping column comprising a stationary phase;
(x) eluting the second portion of the sample captured on the second trapping column off the second trapping column;
(xi) subjecting the second portion of the sample captured on the second trapping column to further separation by SFC.

Embodiment 35

In a further embodiment of any one of embodiments 22 to 34, the RPLC column comprises a reversed-phase stationary phase.

Embodiment 36

In a further embodiment of any one of embodiments 22 to 35, the stationary phase in the trapping column comprises a reversed-phase material.

Embodiment 37

In a further embodiment of any one of embodiments 22 to 36, further separation by SFC is performed on a SFC column comprising a normal phase stationary phase.

Embodiment 38

In a further embodiment of any one of embodiments 22 to 36, further separation by SFC is performed on a SFC system comprising an array of SFC columns.

Embodiment 39

In a further embodiment of embodiment 38, each of the SFC columns independently comprises a normal phase stationary phase.

Embodiment 40

In a further embodiment of embodiment 39, further comprising routing the portion of the sample captured on the trapping column to a SFC column for further separation, said SFC column comprises a stationary phase adapted for separating the components in the sample.

Embodiment 40A

In a further embodiment of embodiment 22, comprising routing the portion of the sample captured on the trapping column to a SFC column for further separation, said SFC column comprises a stationary phase adapted for separating the components in the sample.

Embodiment 41

In one embodiment, the invention provides a method for analyzing a sample using a chromatography system of Embodiment 1 comprising: separating the complex sample into a first set of fractions by reversed-phase liquid chromatography (RPLC) on the first separation unit; and further separating one or more of the fractions by supercritical fluid chromatography (SFC) on the second separation unit.

Embodiment 42

In a further embodiment of embodiment 41, separation by RPLC on the first separation unit is based in part on a first characteristic of the complex sample and separation by SFC on the second separation unit is based in part on a second characteristic of the complex sample, said second characteristic of the complex sample is different from the first characteristic of the complex sample.

Embodiment 43

In a further embodiment of embodiment 41, the complex sample comprises a mixture of stereoisomeric components.

Embodiment 44

In a further embodiment of embodiment 43, the diastereomeric components are separated into one or more fractions by RPLC on the first separation unit, each said fraction comprising an enantiomeric pair.

Embodiment 45

In a further embodiment of embodiment 44, separation by RPLC on the first separation unit is based in part on the hydrophobicity of the complex sample.

Embodiment 46

In a further embodiment of embodiment 44 or 45, the enantiomeric pair is further separated into individual enantiomers by SFC on the second separation unit.

Embodiment 47

In a further embodiment of embodiment 46, separation by SFC on the second separation unit is based in part on the chirality of the complex sample.

Embodiment 48

In one embodiment, the invention provides a method for achiral-chiral analysis of a sample comprising a mixture of stereoisomeric components using a chromatography system of Embodiment 1 comprising: separating one or more diastereomeric component(s) of interest in the sample by RPLC on the first separation unit; and separating the enantiomeric pair(s) of interest by SFC on the second separation unit in the same analytical run.

Embodiment 49

In a further embodiment of embodiment 48, further comprising determining an achiral purity based on a chromatogram from the RPLC separation and determining a chiral purity based on a chromatogram from the SFC separation.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A chromatography system for separating a sample comprising:
a first separation unit comprising:
   a) a first pump assembly for driving a first mobile phase through the first separation unit,
   b) a sample injector for introducing a sample to the first separation unit; and
   c) a reversed-phase liquid chromatography (RPLC) column;
a second separation unit comprising:
   a) a second pump assembly for driving a second mobile phase through the second separation unit, and
   b) a supercritical fluid chromatography (SFC) column; and,
a first fluidic routing unit comprising a plurality of sample loops, said first fluidic routing unit is connected to the first separation unit and the second separation unit,
   wherein at least one of the plurality of sample loops comprises a trapping column, said trapping column comprising a stationary phase; and
   wherein the chromatography system is configured for first separating the sample in the first separation unit and subsequently introducing at least a portion of the sample eluted from the RPLC column of the first separation unit to the second separation unit.

2. The chromatography system of claim 1, wherein the first fluidic routing unit comprises two sample loops; wherein one of the two sample loops is in fluidic communication with the first separation unit and the other one of the two sample loops is in fluidic communication with the second separation unit.

3. The chromatography system of claim 1, wherein the first fluidic routing unit comprises at least three sample loops, and wherein at least one of the sample loops is in fluidic isolation from the first separation unit and the second separation unit.

4. The chromatography system of claim 3, wherein at least one sample loop comprising a stationary phase material is in fluidic isolation from the first separation unit and the second separation unit.

5. The chromatography system of claim 1, wherein the first fluidic routing unit comprises a plurality of trapping columns each positioned in a sample loop.

6. The chromatography system of claim 1, wherein the first fluidic routing unit is configured to allow fluid flow through a sample loop in a first direction when said sample loop is positioned in fluidic communication with the first separation unit and to allow fluid flow through said sample loop in a direction opposite to the first direction when said sample loop is positioned in fluidic communication with the second separation unit.

7. The chromatography system of claim 1, wherein the first fluidic routing unit is configured to allow fluid flow through a sample loop in a first direction when said sample loop is positioned in fluidic communication with the first separation unit and to allow fluid flow through said sample loop in a direction same as the first direction when said sample loop is positioned in fluidic communication with the second separation unit.

8. The chromatography system of claim 1, wherein the RPLC column comprises a reversed-phase stationary phase.

9. The chromatography system of claim 8, wherein the reversed-phase stationary phase comprises a C-18 phase.

10. The chromatography system of claim 8, wherein the stationary phase in the trapping column comprises a reversed-phase material.

11. The chromatography system of claim 9, wherein the reversed-phase material comprises a C-18 phase.

12. The chromatography system of claim 1, wherein the second separation unit comprises one SFC column.

13. The chromatography system of claim 12, wherein the SFC column comprises a normal phase stationary phase.

14. The chromatography system of claim 13, wherein the normal phase stationary phase comprises a silica gel.

15. The chromatography system of claim 1, wherein the second separation unit further comprises a focus column located upstream of the SFC column.

16. The chromatography system of claim 15, wherein the focus column comprises a reversed-phase material.

17. The chromatography system of claim 1, wherein the second separation unit comprises:
   a) an array of SFC columns, wherein the SFC columns in the array are arranged in a parallel configuration; and
   b) a second fluidic routing unit for directing flow of the second mobile phase to a pre-identified SFC column in the array.

18. The chromatography system of claim 17, wherein the second separation unit further comprises a focus column located upstream of each SFC column in the array of SFC columns.

19. The chromatography system of claim 1, further comprising a first detector positioned downstream of the RPLC column.

20. The chromatography system of claim 1, further comprising a second detector positioned downstream of the SFC column.

21. The chromatography system of claim 1, further comprising at least one control device operably connected to one or more of:
   a) the first pump assembly;
   b) the sample injector;
   c) the first detector;
   d) the first fluidic routing unit;
   e) the second pump assembly; and
   f) the second detector.

* * * * *